United States Patent

Bernardon

[11] Patent Number: 5,952,382
[45] Date of Patent: *Sep. 14, 1999

[54] ADAMANTYL-SUBSTITUTED RETINOIDS AND PHARMACEUTICAL/COSMETIC COMPOSITIONS COMPRISED THEREOF

[75] Inventor: Jean-Michel Bernardon, Le Rouret, France

[73] Assignee: Centre International De Recherches Dermatologiques Galderma, Valbonne, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/642,424

[22] Filed: May 3, 1996

[30] Foreign Application Priority Data

May 3, 1995 [FR] France .................................... 95 05279

[51] Int. Cl.⁶ ........................... A61K 31/19; C07C 62/06
[52] U.S. Cl. .......................... 514/569; 562/466; 562/469; 562/473
[58] Field of Search ................... 562/466, 469, 562/473; 560/56, 59, 64, 73; 564/307; 568/808; 544/154, 380; 546/203; 514/569, 828, 849, 845, 859, 861, 863, 871, 238.8, 255, 319

[56] References Cited

U.S. PATENT DOCUMENTS 5,124,473  6/1992  Shroot et al. ............................. 560/56
5,574,036  11/1996  Bernardon et al. ................. 514/239.2

FOREIGN PATENT DOCUMENTS 0210929   2/1987   European Pat. Off. .
0409740   1/1991   European Pat. Off. .
0658553   6/1995   European Pat. Off. .
WO/94/1288  6/1994   WIPO .

OTHER PUBLICATIONS

J. Pharm. Belg., 1994, 221–5, Shroot et al.
Biochem. Biophys. Res. Commun, 1992, 977–83, Bernard et al.
Lee et al, *Proc. Natl. Acad. Sci., USA,* 91:5632–5636 (1994).
Lee et al., *J. Biol. Chem.,* 271(20):11897–11903 (1996).
Yoshimura et al, *J. Med. Chem.,* 38:3163–3173 (1995).

*Primary Examiner*—Alan L. Rotman
*Assistant Examiner*—Charanjit S. Aulakh
*Attorney, Agent, or Firm*—Burns, Doane, Swecker & Mathis, L.L.P.

[57] ABSTRACT

Pharmaceutically/cosmetically-active adamantyl-substituted retinoid compounds have the structural formula (I):

(1)

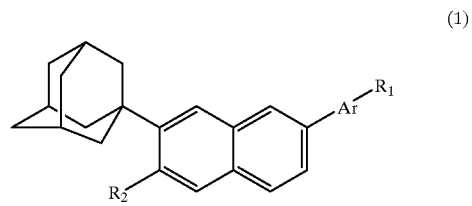

wherein Ar is a radical having one of the formula (a) - (d):

(a)

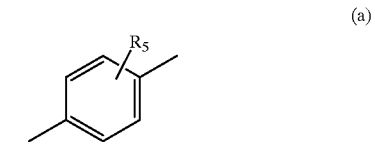

(b)

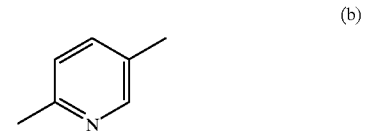

(c)

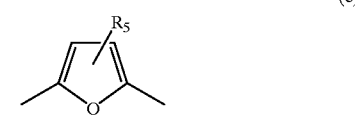

(d)

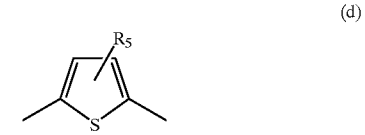

and are useful for the treatment of disorders and/or ailments manifesting an overregulation of RAR receptors and/or a hypervitaminosis A.

53 Claims, No Drawings

ADAMANTYL-SUBSTITUTED RETINOIDS AND PHARMACEUTICAL/COSMETIC COMPOSITIONS COMPRISED THEREOF

CROSS-REFERENCE TO COMPANION APPLICATION

Serial No. 08/429,045, filed Apr. 26, 1995 and assigned to the assignee hereof.

BACKGROUND OF THE INVENTION

1. Technical Field of the Invention

The present invention relates to certain adamantyl compounds of retinoid type and to pharmaceutical/cosmetic compositions comprised thereof; the subject compounds are especially useful for the treatment of disorders and/or ailments manifesting an overregulation of RAR receptors and/or a hypervitaminosis A.

2. Description of the Prior Art

It is known to this art that retinoic acid and certain of its analogs (also deemed retinoids) are capable of inducing differentiation of embryonic teratocarcinoma cells (F9) in mice. Secretion of the plasminogen activator which accompanies this differentiation is an index of the biological response of F9 cells to retinoids. It is also known that the ability of these retinoids to induce the plasminogen activator directly correlates with the affinity which they have for RAR (retinoic acid receptors) receptors endogenous to F9 cells (*Skin Pharmacol.*, 3 pp. 256–267 (1990)).

It is also known that dermatological, rheumatic, respiratory, cardiovascular, osseous or ophthalmological disorders or ailments are in particular related to an overregulation (overexpression or overactivity) of RAR receptors and/or to a hypervitaminosis A (presence in the body of an abnormal amount of vitamin A or of its metabolites). Thus, need continues to exist for compounds which will inhibit the biological effects of an overregulation of RAR receptors and/or of a hypervitaminosis A.

SUMMARY OF THE INVENTION

It has now surprisingly and unexpectedly been determined that certain adamantyl compounds of retinoid type do not induce differentiation of F9 cells but, however, become bound to RARs, this binding being of the antagonist type.

Thus, the present invention features the formulation of an effective amount of at least one compound of retinoid type of the following formula (I) into pharmaceutical/cosmetic compositions for the treatment of disorders or ailments related to an overregulation of RAR receptors and/or to a hypervitaminosis A.

The subject compounds have the following structural formula (I):

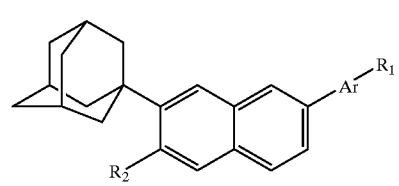

(1)

in which $R_1$ is (i) the —$CH_3$ radical, (ii) the —$CH_2OH$ radical, (iii) an —O—$R_3$ radical, or (iv) a —CO—$R_4$ radical, wherein $R_3$ and $R_4$ are as defined below; Ar is a radical selected from among those of the following formulae (a)-(d):

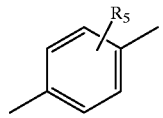   (a)

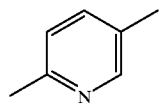   (b)

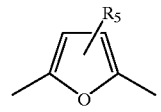   (c)

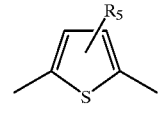   (d)

wherein $R_5$ is as defined below; $R_2$ is an —$(X)_n$—$(CH_2)_p$—$R_6$ radical, an —$(X)_n$—$(CH_2)_q$—$R_7$ radical, a —CH=CH—$(CH_2)_s$—$R_6$ radical, or a —CH=CH—$(CH_2)_t$—$R_7$ radical, wherein $R_6$, $R_7$, x, n, p, a, s and t are as defined below; $R_3$ is a hydrogen atom, a lower alkyl radical, or a —$(CH_2)_m$—$(CO)_n$—$R_8$ radical, wherein $R_8$, m and n are as defined below; $R_4$ is a hydrogen atom, a lower alkyl radical, a radical of the formula:

or an —$OR_9$ radical, wherein R', R" and $R_9$ are as defined below; $R_5$ is a hydrogen or halogen atom, a linear or branched alkyl radical having from 1 to 20 carbon atoms, a hydroxyl radical or an —$OR_{10}$ or —$OCOR_{10}$ radical, wherein $R_{10}$ is as defined below; $R_6$ is a hydrogen atom, a linear or branched alkyl radical having from 1 to 20 carbon atoms, an alkenyl radical, or an alkynyl radical; $R_7$ is an aryl radical, a mono- or polyhydroxyalkyl radical in which the hydroxyl moieties are optionally protected in the methoxy or acetoxy or acetonide form, an aminoalkyl radical in which the amine functional group is optionally substituted by one or two lower alkyl radicals, a polyether radical, a —$COR_4$ radical, a saturated or unsaturated heterocycle, or an aminoaryl radical; $R_8$ is a lower alkyl radical or a saturated heterocycle; $R_9$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; $R_{10}$ is a lower alkyl radical; X is an oxygen atom or an —S(O)$_r$ radical; R' and R", which may be identical or different, are each a hydrogen atom, a lower alkyl radical, a mono- or polyhydroxyalkyl radical, an optionally substituted aryl radical, or an amino acid, peptide or sugar residue, or alternatively, taken together, form a saturated heterocycle, with the proviso that R' and R" may together form, with the nitrogen atom from which they depend, a saturated heterocycle; m is an integer ranging from 1 to 3, inclusive; n is an integer ranging from 0 to 1, inclusive; p is an integer ranging from 5 to 12, inclusive; q is an integer ranging from 0 to 12, inclusive; r is an integer ranging from 0 to 2, inclusive; s is an integer ranging from 3 to 10, inclusive; t is an integer ranging from 0 to 10 inclusive; and the salts and chiral and geometric isomers thereof.

The compounds of formula (I) can therefore also be salts, when $R_1$ or $R_7$ represents a carboxylic acid functional group or when $R_7$ represents an amine functional group, as well as the chiral (optical) and geometric isomers thereof. When the compounds according to the invention exist in the form of salts, they are preferably salts of an alkali metal or alkaline earth metal, or, alternatively, of zinc or of an organic amine.

DETAILED DESCRIPTION OF BEST MODE AND PREFERRED EMBODIMENTS OF THE INVENTION

More particularly according to the present invention, by "lower alkyl radical" is intended a radical having from 1 to 6 carbon atoms and preferably the methyl, ethyl, isopropyl, butyl, tert-butyl and hexyl radicals.

By "linear or branched alkyl radical having from 1 to 20 carbon atoms" is preferably intended methyl, ethyl, propyl, 2-ethylhexyl, octyl, dodecyl, hexadecyl and octadecyl radicals.

By "monohydroxyalkyl radical" is preferably intended a radical having from 1 to 6 carbon atoms, in particular a hydroxymethyl, 2-hydroxyethyl, 2-hydroxypropyl or 3-hydroxypropyl radical.

By "polyhydroxyalkyl radical" is preferably intended to radical having from 3 to 6 carbon atoms and from 2 to 5 hydroxyl groups, such as the 2,3-dihydroxypropyl, 2,3,4-trihydroxybutyl and 2,3,4,5-tetrahydroxypentyl radicals, or the pentaerythritol residue.

By "aryl radical" is preferably intended a phenyl radical optionally substituted by at least one halogen atom, or at least one hydroxyl or nitro functional group.

By "aminoaryl radical" is preferably intended an aminophenyl radical optionally substituted by at least one halogen atom, or at least one hydroxyl or nitro functional group.

By "aralkyl radical" is preferably intended a benzyl or phenethyl radical optionally substituted by at least one halogen atom, or at least one hydroxyl or nitro functional group.

By "alkenyl radical" is intended a radical preferably having from 2 to 5 carbon atoms and having one or more sties of ethylenic unsaturation, for example the allyl radical.

By "sugar residue" is intended a residue derived, in particular, from glucose, galactose or mannose, or from glucuronic acid.

By "amino acid residue" is intended, in particular, a residue derived from lysine, glycine or aspartic acid and by "peptide residue" is intended, mean more particularly, a dipeptide or tripeptide residue prepared via the combination of amino acids.

By "saturated heterocycle" is preferably intended a piperidino, morpholino, pyrrolidino or piperazino radical, optionally substituted in the 4 position by a $C_1$–$C_6$ alkyl or mono- or polyhydroxyalkyl radical as defined above.

By "unsaturated heterocycle" is preferably intended a pyridine, furan or thiophene radical.

The "halogen atoms" are preferably fluorine, chlorine or bromine atoms.

By "aminoalkyl radical" is intended a radical preferably having from 1 to 6 carbon atoms, in particular the aminomethyl, 3-aminopropyl and 6-aminohexyl radicals.

By "polyether radical" is intended a radical preferably having from 1 to 6 carbon atoms, in particular the methoxymethoxy, methoxyethoxy, methoxyethoxymethoxy, methoxymethoxyethyl, methoxymethoxypropyl and methoxyhexyloxy radicals.

Lastly, by "alkynyl radical" is intended a radical preferably having from 2 to 6 carbon atoms, in particular a propargyl radical.

When the radical $R_5$ is a halogen atom, it is preferably a fluorine, bromine or chlorine atom.

Among the compounds of formula (I), particularly representative are the following:

2-Hydroxy-4-[7-(1-adamantyl)-6-benzyloxy-2-naphthyl]benzoic acid;

2-Hydroxy-4-[7-(1-adamantyl)-6-hexyloxy-2-naphthyl]benzoic acid;

4-[7-(1-Adamantyl)-6-methoxyethoxymethoxy-2-naphthyl]benzoic acid;

5-[7-(1-Adamantyl)-6-benzyloxy-2-naphthyl]-2-thiophenecarboxylic acid;

4-[7-(1-Adamantyl)-6-benzyloxy-2-naphthyl]benzoic acid. 4-[7-(1-Adamantyl)-benzyloxycarbonyl-2-naphthyl]benzoic acid;

2-Hydroxy-4-[7-(1-adamantyl)-6-(4-fluorobenzyl)oxy-2-naphthyl]benzoic acid;

6-[7-(1-Adamantyl)-6-methoxyethoxymethoxy-2-naphthyl]nicotinic acid;

4-[7-(1-Adamantyl)-6-heptyloxy-2-naphthyl]benzoic acid;

2-Hydroxy-4-[7-(1-adamantyl)-6-methoxyethoxymethoxy-2-naphthyl]benzoic acid;

2-Chloro-4-[7-(1-adamantyl)-6-methoxyethoxymethoxy-2-naphthyl]benzoic acid;

4-[7-(1-Adamantyl)-6-hydroxyhexyloxy-2-naphthyl]benzoic acid;

4-[7-(1-Adamantyl)-6-hydroxypropyl-2-naphthyl]benzoic acid;

4-[7-(1-Adamantyl)-6-hydroxyoctyloxy-2-naphthyl]benzoic acid;

4-[7-(1-Adamantyl)-6-hydroxyethyl-2-naphthyl]benzoic acid;

4-[7-(1-Adamantyl)-6-hydroxyheptyloxy-2-naphthyl]benzoic acid;

4-[7-(1-Adamantyl)-6-hydroxypentyloxy-2-naphthyl]benzoic acid;

4-[7-(1-Adamantyl)-6-(4-morpholino)ethyloxy-2-naphthyl]benzoic acid;

4-[7-(1-Adamantyl)-6-(1-piperidino)ethyloxy-2-naphthyl]benzoic acid;

4-[7-(1-Adamantyl)-6-carbonylpentyloxy-2-naphthyl]benzoic acid;

4-[7-(1-Adamantyl)-6-ethoxycarbonylpentyloxy-2-naphthyl]benzoic acid;

4-[7-(1-Adamantyl)-6-ethoxycarbonylbutyloxy-2-naphthyl]benzoic acid;

4-[7-(1-Adamantyl)-6-carboxypentyloxy-2-naphthyl]benzoic acid;

4-[7-(1-Adamantyl)-6-carboxybutyloxy-2-naphthyl]benzoic acid;

4-[7-(1-Adamantyl)-6-methoxyethoxymethoxy-2-naphthyl]benzenemethanol;

4-[7-(1-Adamantyl)-6-methoxyethoxymethoxy-2-naphthyl]benzaldehyde;

4-[7-(1-Adamantyl)-6-methoxyethoxymethoxy-2-naphthyl]benzoic acid morpholide;

N-Ethyl-4-[7-(1-adamantyl)-6-methoxyethoxymethoxy-2-naphthyl]benzamide;

4-[7-(1-Adamantyl)-6-methoxyethoxymethoxy-2-naphthyl]benzamide;

N-(4-Hydroxyphenyl)-4-[7-(1-adamantyl)-6-methoxyethoxymethoxy-2-naphthyl]benzamide;

4-[7-(1-Adamantyl)-6-methoxyethoxymethoxy-2-naphthyl]benzoylpiperazine;

Propyl 4-[7-(1-adamantyl)-6-methoxyethoxymethoxy-2-naphthyl]benzoate;

4-[7-(1-Adamantyl)-6-methoxyethoxymethoxy-2-naphthyl]phenyl acetate;

4-[7-(1-Adamantyl)-6-methoxyethoxymethoxy-2-naphthyl]phenol;

4-[7-(1-Adamantyl)-6-methoxyethoxymethoxy-2-naphthyl]phenoxyethylmorpholine hydrochloride;

4-[7-(1-Adamantyl)-6-methoxyethoxymethoxy-2-naphthyl]phenoxyethylpiperidine hydrochloride;

Hexyl 4-[7-(1-adamantyl)-6-methoxyethoxymethoxy-2-naphthyl]benzoate;

N-[[4-[7-(1-Adamantyl)-6-methoxyethoxymethoxy-2-naphthyl]benzoyl]]glutamic acid;

4-[7-(1-Adamantyl)-6-methoxyhexyloxy-2-naphthyl]benzoic acid;

4-[7-(1-Adamantyl)-6-methoxymethoxypropyl-2-naphthyl]benzoic acid;

4-[7-(1-Adamantyl)-6-methoxymethoxyethyl-2-naphthyl]benzoic acid.

According to the present invention, the more particularly preferred compounds of formula (I) are those in which:

$R_1$ is a —CO—$R_4$ radical, $R_2$ is a —$(X)_n(CH_2)_p$—$R_6$ or —$(X)_n$—$(CH_2)_q$—$R_7$ radical, Ar is a radical of formula (a) or (b).

Very particularly preferred compounds of formula (I) are those in which $R_7$ is a polyether radical having a carbon in the position a to the carbon which is in the 6 position of the naphthyl radical. These compounds are very advantageous because they do not appear to be subject to metabolic modification when administered, to compounds of retinoid type which induce differentiation of these F9 cells and which become bound to RARs, this binding being of the agonist type.

The present invention thus features these specific compounds of formula (I) in which $R_7$ is a polyether radical having a carbon in the position a to the carbon which is in the 6 position of the naphthyl radical, such as, in particular, the methoxymethoxyethyl and methoxymethoxypropyl radicals.

Among these specific novel compounds, 4-[7-(1-adamantyl)-6-methoxymethoxy-propyl-2-naphthyl]benzoic acid and 4-[7-(1-adamantyl)-6-methoxymethoxyethyl-2-naphthyl]benzoic acid are the preferred.

The compounds of formula (I) are advantageously prepared:

Either by a coupling reaction between a halogenated derivative (1) and a halogenated derivative (2):

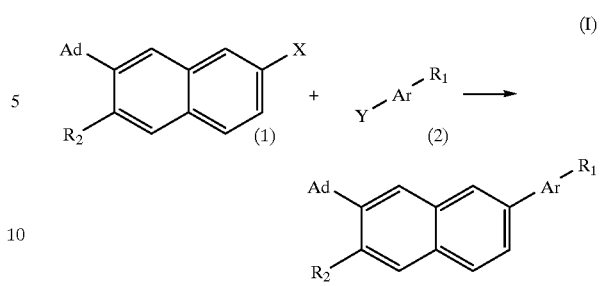

wherein X and Y are each a chlorine, bromine or iodine atom. In a first step, the halide (1) is converted to a lithium or magnesium derivative and then to a zinc derivative and is coupled to the derivative (2) in the presence of a nickel or palladium catalyst, according to the biaryl coupling conditions described by E. Negishi et al, *J. Org. Chem.*, 42, 1821 (1977).

Or by a coupling reaction between a boronic acid (3) and a halogenated derivative (2):

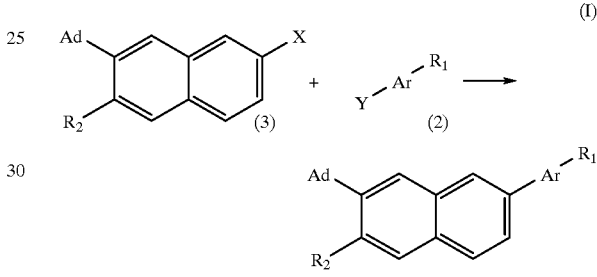

The coupling reaction is carried out in the presence of a palladium catalyst, for example tetrakis(triphenylphosphine) palladium, according to the conditions described by N. Miyaura et al, *Synthetic Communications*, 11 (7), 513–519 (1981). The boronic acid derivative (3) can be obtained, for example, from the halogenated derivative (1) by conversion to a lithium derivative, and then reactomg sa,e with trimethyl borate and hydrolysis.

In these formulae, $R_1$, $R_2$ and $R_5$ are as defined above for the general formula (I) or are derivatives thereof which are suitably protected in order to be compatible with the coupling conditions.

In particular, when $R_1$ is the —COOH radical, the compounds are prepared by protecting $R_1$ with a protective group of alkyl, allyl, benzyl or tert-butyl type.

Conversion to the free form can be carried out:

(1) in the case of an alkyl protective group, by means of sodium hydroxide or of lithium hydroxide in an alcoholic solvent, such as methanol, or in $THF_r$;

(2) in the case of an allyl protective group, by means of a catalyst such as certain transition metal complexes in the presence of a secondary amine, such as morpholine;

(3) in the case of a benzyl protective group, by debenzylation in the presence of hydrogen by means of a catalyst, such as palladium-on-charcoal;

(4) in the case of a protective group of tert-butyl type, by means of trimethylsilyl iodide.

When $R_2$ is the —$(CH_2)_p$—$R_6$, —$(CH_2)_q$—$R_7$, —CH=CH—$(CH_2)_s$—$R_6$ or —CH=CH—$(CH_2)_t$—$R_7$ radicals, the compounds can be obtained from the corresponding phenol derivatives (with $R_2$ representing the —OH radical), which are converted to triflate derivatives and then by nucleophilic substitution in the presence of a palladium catalyst according to the general conditions described by:

S. Cacchi et al, *Tetrahedron Letters*, 27, 3931–3934 (1986);

W. J. Scott et al, *J. Org. Chem.*, 50, 2302–2308 (1985);

J. K. Stille et al, *J. Am. Chem. Soc.*, 109, 5478–5486 (1987).

The cosmetic or pharmaceutical compositions containing at least one compound of formula (I) are suited for the treatment of disorders or ailments related to an overregulation of RAR receptors and/or to a hypervitaminosis A.

By "Overregulation of RAR receptors" according to the invention is intended an overexpression of RAR receptors and/or a biological overactivity of RAR receptors.

The biological overactivity of RAR receptors can be due to a chemical modification of the RAR receptors, but it can also be due to a factor other than the receptor itself. Thus, the biological overactivity can be due to the overexpression of an endogenous gene or to the expression of an exogenous gene comprising the RARE (retinoic acid response element) response element to which a heterodimer comprising the RAR receptor becomes bound, the latter bearing an agonist ligand. Exemplary, of the overexpression of an endogenous gene comprising the RARE response element, is the CRABP II (cellular retinoic acid binding protein II) gene, the overexpression of which has been demonstrated in psoriasis ("Overexpression of CRABP II and down-regulation of CRABP I in psoriatic skin", G. Siegenthaler et al, *Dermatology*, 185, 251–256 (1992)). And exemplary, of the expression of an exogenous gene comprising the RARE response element, is the HIV-1 (human immunodeficiency virus) genome (*Proc. Natl. Acad. Sci.*, USA, Lee et al, Vol. 91, pp. 5632–5636, June 1994) or the genome of the hepatitis B virus ("Retinoid X receptor RXR alpha binds to and trans-activates the hepatitis B virus enhancer", B. Huan et al, *Proc. Natl. Acad. Sci.*, USA, 89 (19), pp. 9059–63 (1992)).

These disorders and/or ailments related to an overregulation of RAR receptors and/or to a hypervitaminosis A are most often reflected by an inflammatory, allergic and/or immunological component. They are more particularly present in the following pathologies or disorders:

(1) acne vulgaris, comedonic or polymorphic acne, acne rosacea, nodulocystic acne, acne conglobata, senile acne and secondary acnes such as solar, medicinal or occupational acne;

(2) other types of disorders of keratinization, in particular ichthyoses, ichthyosiform conditions, Darrier's disease, palmoplantar keratoderma, leucoplakia and leucoplakiform conditions or cutaneous or mucosal (oral) lichen;

(3) other dermatological conditions associated with a disorder of keratinization manifesting an inflammatory and/or immunoallergic component and, in particular, all forms of psoriasis, whether cutaneous, mucosal or ungual, and even psoriatic rheumatism, or alternatively cutaneous atopy, such as eczema, or respiratory atopy or alternatively gingival hypertrophy;

(4) certain inflammatory conditions which do not manifest disorder of keratinization, such as arthritis;

(5) dermal or epidermal proliferations, whether benign or malignant or whether or not of viral origin, such as common warts, flat warts and epidermodysplasia verruciformis, florid or oral papillomatoses and the proliferations which can be induced by ultraviolet radiation, in particular in the case of basal cell and prickle cell epithelioma;

(6) other dermatological disorders, such as bullous dermatoses and collagen diseases;

(7) certain ophthalmological disorders, in particular corneopathies;

(8) aging of the skin, whether photoinduced or chronologic, or actinic keratoses and pigmentations or any pathology associated with chronologic or actinic aging;

(9) the stigmata of epidermal and/or dermal atrophy induced by local or systemic corticosteroids, or any other form of cutaneous atrophy;

(10) disorders of healing or stretch marks; (11) disorders of the sebaceous function such as hyperseborrhoea of acne or simple seborrhoea;

(12) cancerous or precancerous conditions;

(13) condition of viral origin at the cutaneous or general level (human immunodeficiency virus, HIV-1, or hepatitis B virus);

(14) alopecia;

(15) ailments of the cardiovascular system such as arteriosclerosis.

For the aforesaid therapeutic or pharmaceutical applications, the compounds of formula (I) can advantageously be employed in combination with other compounds displaying a retinoid-type activity, with vitamins D or derivatives thereof, with corticosteroids, with compounds which control free radicals, α-hydroxy or α-keto acids or derivatives thereof, or alternatively with ion channel blockers.

By "vitamins D or derivatives thereof" are intended, for example, derivatives of vitamin $D_2$ or $D_3$ and in particular 1,25-dihydroxyvitamin $D_3$.

By "compounds which control free radicals" are intended, for example, α-tocopherol, superoxide dismutase, ubiquinol or certain metal chelating agents.

By "α-hydroxy or α-keto acids or derivatives thereof" are intended, for example, lactic, malic, citric, glycolic, mandelic, tartaric, glyceric or ascorbic acids or the salts, amides or esters thereof. Lastly, by "ion channel blockers" are intended, for example, minoxidil (2,4-diamino-6-piperidinopyrimidine 3-oxide) and derivatives thereof.

The cosmetic or pharmaceutical composition comprising an effective amount of at least one compound of formula (I), one of its chiral analogs or alternatively one of its salts comprises a cosmetically or pharmaceutically acceptable vehicle, carrier or diluent which is compatible with the mode or regimen of administration thereof.

The effective amount, which of course depends on the treatment desired and on the nature of the compound selected, is thus readily determined by one skilled in this art.

The administration of the compounds according to the invention can be carried out enterally, parenterally, topically or ocularly.

For enteral administration, the medicinal/pharmaceutical compositions may be in the form of tablets, hard gelatin capsules, dragees, syrups, suspensions, solutions, powders, granules, emulsions or polymeric or lipid microspheres or nanospheres or vesicles which permit a controlled release. For parenteral administration, the compositions may be in the form of solutions or suspensions for perfusion or for injection.

The compounds according to the invention are generally administered at a daily dose of approximately 0.01 mg/kg to 100 mg/kg by body weight, and this at the rate or regime of 1 to 3 does per diem.

For topical administration, the subject compositions is are particularly intended for treating the skin and the mucosal membranes and can then be provided in the form of ointments, creams, milks, salves, powders, impregnated pads, solutions, gels, sprays, lotions, suspensions or shampoos. They can also be provided in the form of polymeric or lipid vesicles or nanospheres or microspheres or of polymeric patches and of hydrogels which permit controlled release. These compositions for topical administration can, moreover, be provided either in anhydrous form or in an aqueous form.

For ocular administration, they are principally eye washes.

These compositions for topical or ocular application contain at least one compound of formula (I), or one of its chiral analogs or alternatively one of its salts, at a concentration preferably ranging from 0.001% to 5% by weight with respect to the total weight of the composition.

The compositions according to the invention can additionally contain inert or even pharmacodynamically or cosmetically active additives and adjuvants, or combinations of these additives and adjuvants, and, especially, wetting agents; depigmenting agents such as hydroquinone, azelaic acid, caffeic acid or kojic acid; emollients; hydrating agents such as glycerol, PEG 400, thiamorpholinone and its derivatives or alternatively urea; anti-seborrhoeic or anti-acne agents such as S-carboxymethylcysteine, S-benzylcysteamine, their salts or their derivatives, or benzoyl peroxide; antibiotics such as erythromycin and its esters, neomycin, clindamycin and its esters, or tetracyclines; antifungal agents such as ketoconazole or 4,5-polymethylene-3-isothiazolidones; agents promoting hair regrowth, such as minoxidil (2,4-diamino-6-piperidinopyrimidine 3-oxide) and its derivatives, diazoxide (7-chloro-3-methyl-1,2,4-benzothiadiazine 1,1-dioxide) and phenytoin (5,4-diphenylimidazolidine-2,4-dione); non-steroidal anti-inflammatory agents; carotenoids and especially β-carotene; anti-psoriatic agents such as anthralin and its derivatives; and lastly, eicosa-5,8,11,14-tetraenoic and eicosa-5,8,11-trienoic acids, and esters and amides thereof.

The compositions according to the invention may also contain taste- and flavor-enhancing agents, preservatives such as the esters of para-hydroxybenzoic acid, stabilizing agents, moisture-regulating agents, pH-regulating agents, osmotic pressure-modifying agents, emulsifying agents, UV-A and UV-B screening agents and antioxidants such as α-tocopherol, butylated hydroxyanisole or butylated hydroxytoluene.

In order to further illustrate the present invention and the advantages thereof, the following specific examples are given, it being understood that same are intended only as illustrative and in nowise limitative.

EXAMPLE 1

Preparation of 2-hydroxy-4-[7- (l-adamantyl) -6-benzyloxy-2-naphthyl]benzoic acid (a) Preparation of 7-(1-adamantyl)-6-benzyloxy-2-bromonaphthalene 1.26 g (42 mmol) of sodium hydride (80% in oil) and 50 ml of DMF were introduced into a 3-necked flask, a solution of 12.5 g (35 mmol) of 7-(1-adamantyl)-6-hydroxy-2-bromonaphthalene in 100 ml of DMF was added dropwise and stirring was carried out until gas evolution had ceased. 5 ml (42 mmol) of benzyl bromide were then added and stirring was carried out at room temperature for 2 hours. The reaction mixture was poured into water and extracted with ethyl ether and the organic phase was separated by settling, dried over magnesium sulfate and evaporated. The residue obtained was taken up in ethanol, heated to reflux, cooled, filtered and dried. 12.5 g (80%) of the expected compound were collected, which compound had a melting point of 150°–1° C.

(b) Preparation of 7-(1-adamantyl)-6-benzyloxy-2-naphthylboronic acid 3 g (6.7 mmol) of 7-(1-adamantyl)-6-benzyloxy-2-bromonaphthalene and 50 ml of THF were introduced into a three-necked flask under a stream of nitrogen. 3.2 ml (8 mmol) of n-butyllithium (2.5M in hexane) were added dropwise at −78° C. and stirring was carried out for 15 minutes, at the same temperature. 2.1 g (20 mmol) of trimethyl borate were added and stirring was carried out for 2 hours. 23 ml of hydrochloric acid (1N) were added at −50° C. and the temperature was permitted to increase to room temperature. The reaction mixture was extracted with ethyl ether and the organic phase was separated by settling, dried over magnesium sulfate and evaporated. The residue obtained was triturated in heptane, filtered and dried. 2.8 g (100%) of the expected boronic acid were collected, which acid was used, as is, in the synthesis to follow.

(c) Preparation of methyl 2-hydroxy-4-[7-(1-adamantyl)-6-benzyloxy-2-naphthyl]benzoate 300 mg (8.8 mmol) of tetrakis(triphenyl-phosphine) palladium(0), 50 ml of toluene and 2.46 g (8.8 mmol) of methyl 2-hydroxy-4-iodobenzoate were introduced into a three-necked flask under a stream of nitrogen and stirring was carried out at room temperature for 20 minutes. 5.52 g (13.4 mmol) of 7-(1-adamantyl)-6-benzyloxy-2-naphthylboronic acid and 8.8 ml of an aqueous potassium carbonate solution (2N) were then added and the reaction mixture was heated at reflux for 8 hours. The reaction mixture was evaporated to dryness, the residue was taken up in water and ethyl ether and the organic phase was separated by settling, dried over magnesium sulfate and evaporated. The residue was purified by chromatography on a silica column eluted with a mixture of ethyl acetate and heptane (10/90). 1.65 g (36%) of methyl 2-hydroxy-4-[7-(1-adamantyl)-6-benzyloxy-2-naphthyl]benzoate were obtained.

(d) Synthesis of 2-hydroxy-4-[7-(1-adamantyl)-6-benzyloxy-2-naphthyl]benzoic acid 930 mg (1.8 mmol) of methyl 2-hydroxy-4-[7-(1-adamantyl)-6-benzyloxy-2-naphthyl]benzoate and 100 ml of a 2N methanolic sodium hydroxide solution were introduced into a round-bottomed flask and the reaction mixture was heated at reflux for one hour. The reaction mixture was evaporated to dryness, the residue was taken up in water and acidified to pH 1 with concentrated hydrochloric acid and the solid was filtered. The solid obtained was triturated in ethyl acetate, filtered and dried. 710 mg (79%) of the expected acid were collected, which acid had a melting point of 263°–4° C.

EXAMPLE 2

Preparation of 2-hydroxy-4-[7-(1-adamantyl)-6-hexyloxy-2-naphthyl]benzoic acid (a) Preparation of methyl 2-hydroxy-4-[7-(1-adamantyl)-6-hexyloxy-2-naphthyl]benzoate:

Following the procedure of Example 1(a), but reacting 430 mg (1 mmol) of methyl 2-hydroxy-4-[7-(1-adamantyl)-6-hydroxy-2-naphthyl]benzoate with 180 μl (1.2 mmol) of 6-iodohexane, 280 mg (55%) of methyl 2-hydroxy-4-[7-(1-adamantyl)-6-hexyloxy-2-naphthyl]benzoate were obtained.

(b) Synthesis of 2-hydroxy-4-[7-(1-adamantyl)-6-hexyloxy-2-naphthyl]benzoic acid Following the procedure of Example 1(d), from 100 mg (0.2 mmol) of methyl 2-hydroxy-4-[7-(1-adamantyl)-6- hexyloxy-2-naphthyl]benzoate, 90 mg (92%) of the expected acid were obtained, which acid had a melting point of 281°–3° C.

EXAMPLE 3

Preparation of 4-[7-(1-adamantyl)-6-methoxyethoxymethoxy-2-naphthyl]benzoic acid (a) Preparation of Methyl 4-[7-(1-adamantyl)-6-benzyloxy-2-naphthyl]benzoate Following the procedure of Example 1(c), but reacting 2.8 g (6.7 mmol) of 7-(1-adamantyl)-6-benzyloxy-2-naphthylboronic acid with 950 mg (4.4 mmol) of methyl 4-bromobenzoate, 1.6 g (72%) of the expected compound were obtained.

(b) Preparation of methyl 4-[7-(1-adamantyl)-6-hydroxy-2-naphthyl]benzoate 1.38 g (2.75 mmol) of methyl 4-[7-(1-adamantyl-6-benzyloxy-2-naphthyl]benzoate, 450 mg of palladium-on-charcoal (10%) and 50 ml of dioxane were introduced into a reactor. 5 drops of acetic acid WERE added and hydrogenation WAS carried out at 50° C. and under a pressure of 6.5 bars of hydrogen for 4 hours. The catalyst WAS filtered off and washed two times with 20 ml of dioxane and the filtrates were evaporated. The residue obtained was purified by chromatography on a silica column eluted with a mixture of dichloromethane and hexane (50/50). 980 mg (86%) of methyl 4-[7-(1-adamantyl)-6-hydroxy-2-naphthyl]benzoate were collected in the form of an oil.

(c) Preparation of methyl 4-[7-(1-adamantyl)-6-methoxyethoxymethoxy-2-naphthyl]benzoate Following the procedure of Example 1(a), but reacting 980 mg (2.4 mmol) of methyl 4-[7-(1-adamantyl)-6-hydroxy-2-naphthyl]benzoate with 330 $\mu$l (28.6 mmol) of methoxyethoxymethyl chloride, 650 mg (55%) of the expected compound were obtained in the form of an oil.

(d) Synthesis of 4-[7-(1-adamantyl)-6-methoxyethoxymethoxy-2-naphthyl]benzoic acid Following the procedure of Example 1(d), from 650 mg (1.3 mmol) of methyl 4-[7-(1-adamantyl)-6-methoxyethoxymethoxy-2-naphthyl]benzoate, 580 mg (92%) of the expected acid were obtained, which acid had a melting point of 234°–6° C.

EXAMPLE 4

Preparation of 5-[7-(1-adamantyl)-6-benzyloxy-2-naphthyl]-2-thiophenecarboxylic acid (a) Preparation of methyl 5-[7-(1-adamantyl)-6-benzyloxy-2-naphthyl]-2-thiophenecarboxylate Following the procedure of Example 1(c), but reacting 1.5 g (3.6 mmol) of 7-(1-adamantyl)-6-benzyloxy-2-naphthylboronic acid with 400 mg (1.8 mmol) of methyl 5-bromo-2-thiophenecarboxylate, 600 mg (65%) of the expected compound were obtained, which compound had a melting point of 170°–1° C.

(b) Synthesis of 5–17-(1-adamantyl)-6-benzyloxy-2-naphthyl-2-thiophenecarboxylic acid Following the procedure of Example 1(d), from 600 mg (1.2 mmol) of methyl 5-[7-(1-adamantyl)-6-benzyloxy-2-naphthyl]-2-thiophenecarboxylate, 460 mg (79%) of the expected acid were obtained, which acid had a melting point of 271°–3° C.

EXAMPLE 5

Preparation of 4-[7-(1-adamantyl)-6-benzyloxy-2-naphthyl]benzoic acid (a) Preparation of methyl 4-[7-(1-adamantyl)-6-benzyloxy-2-naphthyl]benzoate Following the procedure of Example 1(c), but reacting 1.5 g (3.6 mmol) of 7-(1-adamantyl)-6-benzyloxy-2-naphthylboronic acid with 500 mg (1.9 mmol) of methyl 4-iodobenzoate, 320 mg (33%) of the compound were obtained, which compound had a melting point of 170°–3° C.

(b) Synthesis of 4-[7-(1-adamantyl)-6-benzyloxy-2-naphthyl]benzoic acid

Following the procedure of Example 1(d), from 320 mg (0.6 mmol) of methyl 4-[7-(1-adamantyl)-6-benzyloxy-2-naphthyl]benzoate, 195 mg (63%) of the expected acid were obtained, which acid had a melting point of 305°–10° C.

EXAMPLE 6

Preparation of 4-[7-(1-adamantyl)-6-benzyloxycarbonyl-2-naphthyl]benzoic acid (a) Preparation of methyl 4-[7-(1-adamantyl)-6-trifluoromethyl-sulphonyloxy-2-naphthyl]benzoate 2.7 ml (16 mmol) of trifluoromethanesulfonic anhydride were added dropwise to a solution, cooled to −78° C., of 5.5 g (13.3 mmol) of methyl 4-[7-(1-adamantyl)-6-hydroxy-2-naphthyl]benzoate, 3.2 ml (40 mmol) of pyridine and 162 mg of 4-dimethylamino-pyridine in 100 ml of dichloromethane and the reaction mixture was stirred at room temperature for 12 hours. The reaction mixture was poured into ice-cold water and extracted with ethyl ether and the organic phase was separated by settling, washed with a saturated sodium chloride solution, dried over magnesium sulfate and evaporated.

The residue obtained was purified by chromatography on a silica column eluted with a mixture of ethyl acetate and heptane (10/90). 1.94 g (27%) of methyl 4-[7-(1-adamantyl)-6-trifluoromethylsulfonyloxy-2-naphthyl]benzoate were collected, which compound had a melting point of 226°–7° C.

(b) Preparation of methyl 4-[7-(1-adamantyl)-6-benzyloxycarbonyl-2-naphthyl]benzoate A solution of 1.91 g (3.5 mmol) of methyl 4-[7-(1-adamantyl)-6-trifluoromethylsulfonyloxy-2-naphthyl]benzoate in 50 ml of DMF, 980 $\mu$l (7 mmol) of triethylamine, 39 mg of palladium acetate, 195 mg (0.35 mmol) of 1,11-bis(diphenylphosphino)ferrocene and 3.65 ml (35.1 mmol) of benzyl alcohol were introduced successively into a reactor. The reaction mixture was heated at 80° C. under a pressure of 2.5 bars of carbon monoxide for 12 hours. The reaction mixture was poured into a saturated sodium chloride solution and extracted with ethyl ether and the organic phase was separated by settling, dried over magnesium sulfate and evaporated.

The residue obtained was purified by chromatography on a silica column eluted with a mixture of ethyl acetate and heptane (15/85). After evaporation of the solvents, 720 mg (40%) of the expected compound were collected, which compound had a melting point of 143°–4° C.

(c) Preparation of 4-[7-(1-adamantyl)-6-benzyloxycarbonyl-2-naphthyl]benzoic acid Following the procedure of Example 1(d), from 260 mg (0.5 mmol) of methyl 4-[7-(1-adamantyl)-6-benzyloxycarbonyl-2-naphthyl]benzoate, 200 mg (79%) of the expected acid were obtained, which acid has the melting point 224–6° C.

EXAMPLE 7

Preparation of 2-hydroxy-4-[7-(1-adamantyl)-6-(4-fluoro-benzyl)oxy-2-naphthyl]benzoic acid (a) Preparation of 7-(1-adamantyl)-6-(4-fluorobenzyl)oxy-2-bromonaphthalene Following the procedure of Example 1(a), but reacting 1.1 g (3 mmol) of 7-(1-adamantyl)-6-hydroxy-2-bromonaphthalene with 420 μl (3.3 mmol) of 4-fluorobenzyl bromide, 1.2 g (86%) of the expected compound were obtained in the form of a colorless oil.

(b) Preparation of 7-(1-adamantyl)-6-(4-fluorobenzyl)oxy-2-naphthylboronic acid

Following the procedure of Example 1(b), from 1.14 g (2.45 mmol) of 7-(1-adamantyl)-6-(4-fluorobenzyl)oxy-2-bromonaphthalene, 560 mg (57%) of the expected boronic acid were obtained.

(c) Preparation of methyl 2-hydroxy-4-[7-(1-adamantyl)-6-(4-fluorobenzyl)oxy-2-naphthyl]benzoate Following the procedure of Example 1(c), but reacting 560 mg (1.41 mmol) of 7-(1-adamantyl)-6-(4-fluorobenzyl)oxy-2-naphthylboronic acid with 330 mg (1.17 mmol) of methyl 2-hydroxy-4-iodobenzoate, 490 mg (78%) of the expected ester were obtained, which ester had a melting point of 189°–91° C.

(d) Synthesis of 2-hydroxy-4-[7-(1-adamantyl)-6-(4-fluorobenzyl)oxy-2-naphthyl]benzoic acid Following the procedure of Example 1(d), from 490 mg (0.91 mmol) of methyl 2-hydroxy-4-[7-(1-adamantyl)-6-(4-fluorobenzyl)oxy-2-naphthyl]benzoate, 440 mg (92%) of the expected acid were obtained, which acid had a melting point of 240°–1° C.

EXAMPLE 8

Preparation of 6-[7-(1-adamantyl)-6-methoxyethoxymethoxy-2-naphthyl]nicotinic acid (a) Preparation of 3-(1-adamantyl)-6-bromo-2-naphthol 56 g (0.25 mol) of 6-bromo-2-naphthol, 38.2 g (0.25 mol) of 1-adamantanol and 500 ml of a mixture of dichloromethane and heptane (40/60) were introduced into a round-bottomed flask. 15 ml of concentrated sulfuric acid were added and the reaction mixture was stirred at room temperature for 48 hours. The solid was filtered off, washed with heptane (3×100 ml) and dissolved in ethyl ether and the organic phase was washed with water, separated by settling, dried over magnesium sulfate and evaporated. 60.1 g (67%) of the expected compound were collected, which compound had a melting point of 215°–6° C.

(b) Preparation of 7-(1-adamantyl)-6-methoxyethoxymethoxy-2-bromonaphthalene 17.85 g (0.05 mol) of 3-(1-adamantyl)-6-bromo-2-naphthol and 200 ml of DMF were introduced into a three-necked flask under a stream of nitrogen. 1.8 g (0.06 mol) of sodium hydride (80% in oil) was added portionwise and the reaction mixture was stirred until gas evolution had ceased. 6.9 ml (0.06 mol) of methoxyethoxymethyl chloride were then added and the reaction mixture was stirred at room temperature for 2 hours. The reaction mixture was poured into ice-cold water and extracted with ethyl ether and the organic phase was separated by settling, dried over magnesium sulfate and evaporated. The residue obtained was purified by chromatography on a silica column eluted with a mixture of dichloromethane and heptane (40/60). 19.5 g (87%) of the expected compound were collected, which compound had a melting point of 99°–100° C.

(c) Preparation of 7-(1-adamantyl)-6-methoxyethoxymethoxy-2-naphthylboronic acid Following the procedure of Example 1(b), from 61.9 g (0.139 mol) of 7-(1-adamantyl)-6-methoxyethoxymethoxy-2-bromonaphthalene, 54 g (95%) of 7-(1-adamantyl)-6-methoxyethoxymethoxy-2-naphthylboronic acid were obtained, which compound had a melting point of 172°–4° C.

(d) Preparation of methyl 6-[7-(1-adamantyl)-6-methoxyethoxymethoxy-2-naphthyl]nicotinate Following the procedure of Example 1(c), but reacting 1.3 g (3.1 mmol) of 7-(1-adamantyl)-6-methoxyethoxymethoxy-2-naphthylboronic acid with 790 mg (3 mmol) of methyl 6-iodonicotinate, 860 mg (57%) of the expected ester were obtained, which ester had a melting point of 166°–7° C.

(e) Synthesis of 6-[7-(1-adamantyl)-6-methoxyethoxymethoxy-2-naphthyl]nicotinic acid Following the procedure of Example 1(d), from 853 mg (1.7 mmol) of the above methyl ester, 790 mg (95%) of the expected acid were obtained, which acid had a melting point of 247°–8° C.

EXAMPLE 9

Preparation of 4-[7-(1-adamantyl)-6-heptyloxy-2-naphthyl]benzoic acid (a) Preparation of 7-(1-adamantyl)-6-heptyloxy-2-bromonaphthalene Following the procedure of Example 8(b), but reacting 3.4 g (9.5 mmol) of 3-(1-adamantyl)-6-bromo-2-naphthol with 2.05 g (11.4 mmol) of 1-bromoheptane, 3.4 g (79%) of 7-(1-adamantyl)-6-heptyloxy-2-bromonaphthalene were obtained.

(b) Preparation of 7-(1-adamantyl)-6-heptyloxy-2-naphthylboronic acid

Following the procedure of Example 1(b), from 3.5 g (17.7 mmol) of 7-(1-adamantyl)-6-heptyloxy-2-bromonaphthalene, 1.67 g (51%) of 7-(1-adamantyl)-6-heptyloxy-2-naphthylboronic acid were obtained.

(c) Preparation of methyl 4-[7-(1-adamantyl)-6-heptyloxy-2-naphthyl]benzoate Following the procedure of Example 1(c), but reacting 1.6 g (3.8 mmol) of 7-(1-adamantyl)-6-heptyloxy-2-naphthylboronic acid with 830 mg (3.17 mmol) of methyl 4-iodobenzoate, 460 mg (29%) of the expected methyl ester were obtained.

(d) Synthesis of 4-[7-(1-adamantyl)-6-heptyloxy-2-naphthyl]benzoic acid

Following the procedure of Example 1(d), from 330 mg (0.65 mmol) of methyl 4-[7-(1-adamantyl)-6-heptyloxy-2-naphthyl]benzoate, 260 mg (81%) of the expected acid were obtained, which acid had a melting point of 266°–7° C.

EXAMPLE 10

Preparation of 2-hydroxy-4-[7-(1-adamantyl)-6-methoxyethoxymethoxy-2-naphthyl]benzoic acid

(a) Preparation of methyl 2-hydroxy-4-[7-(1-adamantyl)-6-methoxyethoxymethoxy-2-naphthyl]benzoate Following the procedure of Example 1(c), but reacting 2.25 g (5.5 mmol) of 7-(1-adamantyl)-6-methoxyethoxymethoxy-2-naphthylboronic acid with 1.39 g (5 mmol) of methyl 2-hydroxy-4-iodobenzoate, 2.1 g (81%) of the expected ester were obtained, which ester had a melting point of 101°–2° C.

(b) Synthesis of 2-hydroxy-4-[7-(1-adamantyl)-6-methoxyethoxy-methoxy-2-naphthyl]benzoic acid Following the procedure of Example 1(d), from 2.08 g (4 mmol) of the methyl ester prepared in step (a), 1.72 g (86%) of the expected acid were obtained, which acid had a melting point of 225°–6° C.

EXAMPLE 11

Preparation of 2-chloro-4-[7-(1-adamantyl)-6-mothoxyethoxy-methoxy-2-naphthyl]benzoic acid

(a) Preparation of methyl 2-chloro-4-[7-(1-adamantyl)-6-methoxyethoxymethoxy-2-naphthyl]benzoate Following the procedure of Example 1(c), but reacting 2.25 g (5.5 mmol) of 7-(1-adamantyl)-6-methoxyethoxymethoxy-2-naphthylboronic acid with 1.48 g (5 mmol) of methyl 2-chloro-4-iodobenzoate, 2.32 g (87%) of the expected ester were obtained, which ester had a melting point of 112°–3° C.

(b) Synthesis of 2-chloro-4-[7-(1-adamantyl)-6-methoxyethoxy-methoxy-2-naphthyl]benzoic acid Following the procedure of Example 1(d), from 2.31 g (4.3 mmol) of the methyl ester prepared in step (a), 1.97 g (88%) of the expected acid were obtained, which acid had a melting point of 190°–2° C.

EXAMPLE 12

Preparation of 4-[7-(1-adamantyl)-6-hydroxyhexyloxy-2-naphthyl]benzoic acid

(a) Preparation of methyl 4-[7-(1-adamantyl)-6-hydroxyhexyloxy-2-naphthyl]benzoate 1.62 g (40 mmol) of methyl 4-[7-(1-adamantyl)-6-hydroxy-2-naphthyl]benzoate, 830 mg of potassium carbonate and 60 ml of methyl ethyl ketone were introduced into a round-bottomed flask under a stream of nitrogen. 1.09 g (60 mmol) of 6-bromo-1-hexanol was added and the reaction mixture was heated at reflux for 12 hours. The reaction mixture was poured into 1N hydrochloric acid and extracted with ethyl ether and the organic phase was separated by settling, dried over magnesium sulfate and evaporated.

The residue obtained was purified by chromatography on a silica column eluted with dichloromethane. After evaporation of the solvents, 1.58 g (77%) of the expected methyl ester were collected, which ester had a melting point of 153°–5° C.

(b) Synthesis of 4-[7-(1-adamantyl)-6-hydroxyhexyloxy-2-naphthyl]benzoic acid Following the procedure of Example 1(d), from 700 mg (1.36 mmol) of methyl 4-[7-(1-adamantyl)-6-hydroxyhexyloxy-2-naphthyl]benzoate, 417 mg (61%) of the expected acid were obtained, which acid had a melting point of 254°–6° C.

EXAMPLE 13

Preparation of 4-[7-(1-adamantyl)-6-hydroxypropyl-2-naphthyl]benzoic acid

(a) Preparation of methyl 4-[7-(1-adamantyl)-6-allyl-2-naphthyl]benzoate 4 g (7.34 mmol) of methyl 4-[7-(1-adamantyl)-6-trifluoromethylsulfonyloxy-2-naphthyl]benzoate, 2.30 ml (7.9 mmol) of allyltributyltin, 630 mg of lithium chloride and 40 ml of DMF were introduced into a three-necked flask under a stream of nitrogen. The reaction mixture was stirred at room temperature for 30 minutes, 104 mg (0.146 mmol) of bis(triphenylphosphine)palladium(II) chloride were added and the reaction mixture was heated at 100° C. for three hours. The reaction mixture was poured into water and extracted with ethyl ether and the organic phase is separated by settling, dried over magnesium sulfate and evaporated.

The residue obtained was purified by chromatography on a silica column, eluted with a mixture of heptane and dichloromethane (50/50). 1.7 g (53%) of the expected compound were collected, which compound had a melting point of 171°–3° C.

(b) Preparation of methyl 4-[7-(1-adamantyl)-6-hydroxypropyl-2-naphthyl]benzoate 1.7 g (3.9 mmol) of methyl 4-[7-(1-adamantyl)-6-allyl-2-naphthyl]benzoate and 40 ml of THF were introduced into a round-bottomed flask under a stream of nitrogen. A solution of 23.5 ml (11.7 mmol) of 9-borabicyclo[3.3.1]nonane (0.5M in THF) was added dropwise at 0° C. and the reaction mixture was stirred for one hour at room temperature. 12 ml (12 mmol) of a sodium hydroxide solution (1 M) and 10 ml of a 30% hydrogen peroxide solution were then added successively and at 0° C. and the reaction mixture was stirred at room temperature for one hour. The reaction mixture was poured into water and extracted with ethyl ether and the organic phase was separated by settling, dried over magnesium sulfate and evaporated.

The white powder obtained was purified by chromatography on a silica column eluted with dichloromethane. 1.67 g (94%) of the expected compound were collected, which compound had a melting point of 184°–6° C.

(c) Synthesis of 4-[7-(1-adamantyl)-6-hydroxypropyl-2-naphthyl]benzoic acid

Following the procedure of Example 1(d), from 500 mg (1.1 mmol) of the above ester, 417 mg (86%) of 4-[7-(1- adamantyl)-6-hydroxypropyl-2-naphthyl]benzoic acid were collected, which acid had a melting point of 268°–9° C.

EXAMPLE 14

Preparation of 4-[7-(1-adamantyl)-6-hydroxyoctyloxy-2-naphthyl]benzoic acid (a) Preparation of methyl 4-[7-(1-adamantyl)-6-hydroxyoctyloxy-2-naphthyl]benzoate Following the procedure of Example 12(a), but reacting 1.5 g (3.6 mmol) of methyl 4-[7-(1-adamantyl)-6-hydroxy-2-naphthyl]benzoate with 930 μl(5.45 mmol) of 1-bromo-8-octanol, 800 mg (41%) of the expected compound were obtained, which compound had a melting point of 120°–1° C.

(b) Synthesis of 4-[7-(1-adamantyl)-6-hydroxyoctyloxy-2-naphthyl]benzoic acid

Following the procedure of Example 1(d), from 630 mg (1.17 mmol) of the ester prepared in step (a), 487 mg (79%) of 4-[7-(1-adamantyl)-6-hydroxyoctyloxy-2-naphthyl] benzoic acid were obtained, which acid had a melting point of 242°–3° C.

EXAMPLE 15

Preparation of 4-[7-(1-adamantyl)-6-hydroxyethyl-2-naphthyl]benzoic acid (a) Preparation of methyl 4-[7-(1-adamantyl)-6-vinyl-2-naphthyl]benzoate Following the procedure of Example 13(a), but reacting 4.82 g (8.86 mmol) of methyl 4-[7-(1-adamantyl)-6-trifluoromethylsulfonyloxy-2-naphthyl]benzoate with 3.90 ml (13.3 mmol) of vinyltributyltin, 805 mg (21.5%) of methyl 4-[7-(1-adamantyl)-6-vinyl-2-naphthyl]benzoate were obtained, which compound had a melting point of 221°–2° C.

(b) Preparation of methyl 4-[7-(1-adamantyl)-6-hydroxyethyl-2-naphthyl]benzoate

Following the procedure of Example 13(b), from 794 mg (1.88 mmol) of methyl 4-[7-(1-adamantyl)-6-vinyl-2-naphthyl]benzoate, 430 mg (54%) of the expected alcohol were obtained, which alcohol had a melting point of 168°–70° C.

(c) Synthesis of 4-[7-(1-adamantyl)-6-hydroxyethyl-2-naphthyl]benzoic acid

Following the procedure of Example 1(d), from 108 mg (0.25 mmol) of the ester prepared in step (b), 60 mg (38%) of 4-[7-(1-adamantyl)-6-hydroxyethyl-2-naphthyl]benzoic acid were collected, which acid had a melting point of 276°–8° C.

EXAMPLE 16

Preparation of 4-[7-(1-adamantyl)-6-hydroxyheptyloxy-2-naphthyl]benzoic acid (a) Preparation of methyl 4-[7-(1-adamantyl)-6-hydroxyheptyloxy-2-naphthyl]benzoate Following the procedure of Example 12(a), but reacting 1.5 g (3.6 mmol) of methyl 4-[7-(1-adamantyl)-6-hydroxy-2-naphthyl]benzoate with 840 μl(5.45 mmol) of 1-bromo-7-heptanol, 1 g (52%) of the expected compound was obtained, which compound had a melting point of 150°–1° C.

(b) Synthesis of 4-[7-(1-adamantyl)-6-hydroxyheptyloxy-2-naphthyl]benzoic acid

Following the procedure of Example 1(d), from 1 g (1.9 mmol) of the methyl ester prepared in step (a), 830 mg (86%) of 4-[7-(1-adamantyl)-6-hydroxyheptyloxy-2-naphthyl]benzoic acid were obtained, which acid had a melting point of 227°–8° C.

EXAMPLE 17

Preparation of 4-[7-(1-adamantyl)-6-hydroxypentyloxy-2-naphthyl]benzoic acid (a) Preparation of methyl 4-[7-(1-adamantyl)-6-acetoxypentyloxy-2-naphthyl]benzoate Following the procedure of Example 12(a), but reacting 1 g (2.4 mmol) of methyl 4-[7-(1-adamantyl)-6-hydroxy-2-naphthyl]benzoate with 760 mg (3.6 mmol) of 5-bromo-pentyl acetate, 1.3 g (100%) of the expected methyl ester were obtained, which ester had a melting point of 132°–3° C.

(b) Synthesis of 4-[7-(1-adamantyl)-6-hydroxypentyloxy-2-naphthyl]benzoic acid

Following the procedure of Example 1(d), from 1.3 g (2.4 mmol) of the ester prepared in step (a), 1 g (79%) of the expected acid was obtained, which acid had a melting point of 271°–2° C.

EXAMPLE 18

Preparation of 4-[7-(1-adamantyl)-6-(4-morpholino) ethyloxy-2-naphthyl]benzoic acid (a) Preparation of methyl 4-[7-(1-adamantyl)-6-(4-morpholino)-ethyloxy-2-naphthyl]benzoate Following the procedure of Example 12(a), but reacting 1.5 g (3.6 mmol) of methyl 4-[7-(1-adamantyl)-6-hydroxy-2-naphthyl]benzoate with 5.45 g (5.45 mmol) of 4-(2-chloroethyl)morpholine hydrochloride, 1.52 g (88%) of the expected methyl ester were obtained, which ester had a melting point of 198°–9° C.

(b) Synthesis of 4-[7-(1-adamantyl)-6-(4-morpholino)ethyloxy-2-naphthyl]benzoic acid Following the procedure of Example 1(d), from 1.45 g (2.76 mmol) of the ester prepared in step (a), 956 mg (68%) of the expected acid were obtained, which acid had a melting point of 280° C. with decomposition.

EXAMPLE 19

Preparation of 4-[7-(1-adamantyl)-6-(1-piperidino) ethyloxy-2-naphthyl]benzoic acid (a) Preparation of methyl 4-[7-(1-adamantyl)-6-(1-piperidino)ethyloxy-2-naphthyl]benzoate Following the procedure of Example 12 (a), but reacting 1.5 g (3.6 mmol) of methyl 4-[7-(1-adamantyl)-6-hydroxy-2-naphthyl]benzoate with 1 g (5.45 mmol) of 1-(2- chloroethyl)piperidine hydrochloride, 1.46 g (77%) of the expected methyl ester were obtained, which ester had a melting point of 240°–1° C.

(b) Synthesis of 4-[7-(1-adamantyl)-6-(1-piperidino) ethyloxy-2-naphthyl]benzoic acid Following the procedure of Example 1(d), from 1.25 g (2.3 mmol) of the above ester prepared in step (a), 640 mg (53%) of the expected acid were obtained, which acid had a melting point of 250° C. with decomposition.

EXAMPLE 20

Preparation of 4-[7-(1-adamantyl)-6-carbonylpentyloxy-2-naphthyl]benzoic acid (a) Preparation of methyl 4-[7-(1-adamantyl)-6-carbonylpentyloxy-2-naphthyl]benzoate Following the procedure of Example 12(a), but reacting 640 mg (1.55 mmol) of methyl 4-[7-(1-adamantyl)-6-hydroxy-2-naphthyl]benzoate with 450 mg (2.32 mmol) of 6-bromohexanamide, 520 mg (65%) of the expected compound were obtained, which compound had a melting point of 209°–10° C.

(b) Synthesis of 4-[7-(1-adamantyl)-6-carbonylpentyloxy-2-naphthyl]benzoic acid

Following the procedure of Example 1(d), from 400 mg (0.76 mmol) of the ester prepared in step (a), 350 mg (90%) of the expected acid were obtained, which acid had a melting point of 270°–10° C.

EXAMPLE 21

Preparation of 4-[7-(1-adamantyl)-6-ethoxycarbonylpentyloxy-2-naphthyl]benzoic acid (a) Preparation of allyl 4-[7-(1-adamantyl)-6-ethoxycarbonyl-pentyloxy-2-naphthyl]benzoate Following the procedure of Example 12(a), but reacting 3 g (6.8 mmol) of allyl 4-[7-(1-adamantyl)-6-hydroxy-2-naphthyl]benzoate with 2.3 g (10.2 mmol) of ethyl 6-bromohexanoate, 2.15 g (55%) of the expected compound were obtained, which compound had a melting point of 116°–7° C.

(b) Synthesis of 4-[7-(1-adamantyl)-6-ethoxycarbonylpentyloxy-2-naphthyl]benzoic acid 1.5 g (2.58 mmol) of allyl 4-[7-(1-adamantyl)-6-ethoxycarbonylpentyloxy-2-naphthyl]benzoate, 50 ml of THF and 90 mg (0.08 mmol) of tetrakis(triphenylphosphine) palladium(0) were introduced into a three-necked flask under a stream of nitrogen. 1.13 ml (13 mmol) of morpholine were added dropwise and the reaction mixture was stirred at room temperature for two hours. The reaction mixture was evaporated to dryness, the residue was taken up in water, acidified to pH 1 with hydrochloric acid and extracted with ethyl ether and the organic phase was separated by settling, dried over magnesium sulfate and evaporated. The solid was triturated in heptane, filtered and dried. 1 g (72%) of the expected acid was collected, which acid had a melting point of 270°–1° C.

EXAMPLE 22

Preparation 4-[7-(1-adamantyl)-6-ethoxycarbonylbutyloxy-2-naphthyl]benzoic acid (a) Preparation of allyl 4-[7-(1-adamantyl)-6-ethoxycarbonylbutyloxy-2-naphthyl]benzoate Following the procedure of Example 12(a), but reacting 2 g (4.5 mmol) of allyl 4-[7-(1-adamantyl)-6-hydroxy-2-naphthyl]benzoate with 1.4 g (6.7 mmol) of ethyl 5-bromovalerate, 1.55 g (59%) of the expected compound was obtained, which compound had a melting point of 117°–8° C.

(b) Synthesis of 4-[7-(1-adamantyl)-6-ethoxycarbonylbutyloxy-2-naphthyl]benzoic acid Following the procedure of Example 21(b), from 1.48 g (2.6 mmol) of the above ester, 1.19 g (87%) of 4-[7-(1-adamantyl)-6-ethoxycarbonylbutyloxy-2-naphthyl]benzoic acid was obtained, which acid had a melting point of 200° C. with decomposition.

EXAMPLE 23

Preparation of 4-[7-(1-adamantyl)-6-carboxypentyloxy-2-naphthyl]benzoic acid

Following the procedure of Example 1(d), from 690 mg (1.28 mmol) of 4-[7-(1-adamantyl)-6-ethoxycarbonyl-pentyloxy-2-naphthyl]benzoic acid, 250 mg (39%) of the expected acid were obtained, which acid had a melting point of 305°–6° C.

EXAMPLE 24

Preparation of 4-[7-(1-adamantyl)-6-carboxybutyloxy-2-naphthyl]benzoic acid

Following the procedure of Example 1(d), from 730 mg (1.4 mmol) of 4-[7-(1-adamantyl)-6-ethoxycarbonyl-butyloxy-2-naphthyl]benzoic acid, 510 mg (90%) of the expected acid were obtained, which acid had a melting point of 317°–8° C.

EXAMPLE 25

Preparation of 4-[7-(1-adamantyl)-6-methoxyethoxymethoxy-2-naphthyl] benzenemethanol 3 g (6.1 mmol) of 4-[7-(1-adamantyl)-6-methoxyethoxymethoxy-2-naphthyl]benzoic acid and 40 ml of THF were introduced into a three-necked flask under a stream of nitrogen. 20 ml of a solution of borane (1M in THF) were added dropwise and the reaction mixture was heated at 40° C. for one hour. The reaction mixture was poured into a 1N hydrochloric acid solution and extracted with ethyl acetate and the organic phase was separated by settling, dried over magnesium sulfate and evaporated.

The residue obtained was purified by chromatography on a silica column and eluted with a mixture of heptane and ethyl acetate (60/40). 2.44 g (84%) of 4-[7-(1-adamantyl)-6-methoxyethoxymethoxy-2-naphthyl]-benzenemethanol were collected, which compound had a melting point of 131°–2° C.

EXAMPLE 26

Preparation of 4-[7-(1-adamantyl)-6-methoxyethoxymethoxy-2-naphthyl]benzaldehyde 2.63 g (5.9 mmol) of 4-[7-(1-adamantyl)-6-methoxyethoxymethoxy-2-naphthyl]benzenemethanol and 40 ml of dichloromethane were introduced into a round-bottomed flask and 4.2 g of pyridinium dichromate were added. The reaction mixture was stirred at room temperature for twelve hours, was filtered through silica and the filtrate was evaporated. The solid obtained was recrystallized from heptane and 490 mg (19%) of 4-[7-(1-adamantyl)-6-methoxyethoxymethoxy-2-naphthyl]benzaldehyde were collected, which compound had a melting point of 83°–4° C.

EXAMPLE 27

Preparation of 4-[7-(1-adamantyl)-6-methoxyethoxymethoxy-2-naphthyl]benzoic acid morpholide (a) Preparation of 4-[7-(1-adamantyl)-6-methoxyethoxymethoxy-2-naphthyl]benzoic acid chloride 10 g (20.6 mmol) of 4-[7-(1-adamantyl)-6-methoxyethoxymethoxy-2-naphthyl]benzoic acid and 100 ml of dichloromethane were introduced into a round-bottomed flask and 4.3 ml (21.6 mmol) of dicyclohexylamine were added dropwise. The reaction mixture was stirred at room temperature for one hour and 2.2 ml (21.6 mmol) of thionyl chloride were added dropwise. The reaction mixture was stirred for one hour and was evaporated to dryness, the residue was taken up in ethyl ether, the dicyclohexylamine salt was filtered off and the filtrate was evaporated. 10.4 g (100%) of the crude acid chloride were collected, which acid chloride was used as is in the synthesis to follow.

(b) Synthesis of 4-[7-(1-adamantyl)-6-methoxyethoxymethoxy-2-naphthyl]benzoic acid morpholide 1.8 ml (20.6 mmol) of morpholine and 40 ml of THF were introduced into a round-bottomed flask. A solution of 3.5 g (6.9 mmol) of 4-[7-(1-adamantyl)-6-methoxyethoxymethoxy-2-naphthyl]benzoic acid chloride in THF was added dropwise and the reaction mixture was stirred at room temperature for two hours. The reaction mixture was poured into water and extracted with ethyl acetate and the organic phase was separated by settling, dried over magnesium sulfate and evaporated. The solid obtained was triturated in hexane, filtered and dried. 2.8 g (74%) of the expected amide were collected, which amide had a melting point of 86°–7° C.

EXAMPLE 28

Preparation of N-ethyl-4-[7-(1-adamantyl)-6-methoxyethoxymethoxy-2-naphthyl]benzamide Following the procedure of Example 27(b), but reacting 3.5 g (6.9 mmol) of 4-[7-(1-adamantyl)-6-methoxyethoxy-methoxy-2-naphthyl]benzoic acid chloride with 1.7 ml (20.6 mmol) of ethylamine (70%), 2.6 g (75%) of the expected ethyl amide were obtained, which ethyl amide had a melting point of 154°–5° C.

EXAMPLE 29

Preparation of 4-[7-(1-adamantyl)-6-methoxyethoxymethoxy-2-naphthyl]benzamide

Following the procedure of Example 27(b), but reacting 3.5 g (6.9 mmol) of 4-[7-(1-adamantyl)-6-methoxyethoxy-methoxy-2-naphthyl]benzoic acid chloride with 1.5 ml (26.2 mmol) of aqueous ammonia (32%), 2.9 g (89%) of the expected amide were obtained, which amide had a melting point of 198°–9° C.

EXAMPLE 30

Preparation of N-(4-hydroxyphenyl)-4-[7-(1-adamantyl)-6-methoxy-ethoxymethoxy-2-naphthyl]benzamide (a) Preparation of N-(4-acetoxyphenyl)-4-[7-(1-adamantyl)-6-methoxy-ethoxymethoxy-2-naphthyl]benzamide 970 mg (6.4 mmol) of 4-acetoxyaniline, 50 ml of THF and 990 µl (7 mmol) of triethylamine were introduced into a round-bottomed flask. A solution of 3.2 g (6.4 mmol) of 4-[7-(1-adamantyl)-6-methoxyethoxy-methoxy-2-naphthyl]benzoic acid chloride in THF was added dropwise and the reaction mixture was stirred at room temperature for two hours. The reaction mixture was poured into water and extracted with ethyl acetate and the organic phase was separated by settling, dried over magnesium sulfate and evaporated. The residue obtained was triturated in heptane, filtered and dried. 3.15 g (81%) of the expected compound were collected, which compound had a melting point of 206°–7° C.

(b) Synthesis of N-(4-hydroxyphenyl)-4-[7-(1-adamantyl)-6-methoxy-ethoxymethoxy-2-naphthyl]benzamide Following the procedure of Example 1(d), from 3.15 g (5.2 mmol) of N-(4-acetoxyphenyl)-4-[7-(1-adamantyl)-6-methoxyethoxymethoxy-2-naphthyl]benzamide, 2.3 g (77%) of N-(4-hydroxyphenyl)-4-[7-(1-adamantyl)-6-methoxyethoxymethoxy-2-naphthyl]benzamide were obtained, which compound had a melting point of 231°–3° C.

EXAMPLE 31

Preparation of 4-[7-(1-adamantyl)-6-methoxyethoxymethoxy-2-naphthyl]benzoylpiperazine (a) Preparation of N-benzyl-4-[7-(1-adamantyl)-6-methoxyethoxy-methoxy-2-naphthyl]benzoylpiperazine Following the procedure of Example 27(b), but reacting 7.3 g (14.4 mmol) of 4-[7-(1-adamantyl)-6-methoxy-ethoxymethoxy-2-naphthyl]benzoic acid chloride with 2.5 ml (14.4 mmol) of 4-benzylpiperazine, 3 g (33%) of the expected compound were obtained, which compound had a melting point of 176°–7° C.

(b) Synthesis of 4-[7-(1-adamantyl)-6-methoxyethoxymethoxy-2-naphthyl]benzoylpiperazine 500 mg (0.8 mmol) of the amide prepared in step (a) and 20 ml of methanol were introduced into a three-necked flask. 900 mg of Pd/C (10%) and then 900 µl of formic acid were added and the reaction mixture was stirred at room temperature for three hours. The catalyst was filtered off, the filtrate was poured into an aqueous bicarbonate solution and extracted with ethyl acetate and the organic phase was separated by settling, dried over magnesium sulfate and evaporated.

The residue obtained was purified by chromatography on a column of silica and eluted with a mixture of dichloromethane and methanol (80/20). 310 mg (72%) of the expected compound were collected, which compound had a melting point 177°–8° C.

EXAMPLE 32

Preparation of propyl 4-[7-(1-adamantyl)-6-methoxyethoxymethoxy-2-naphthyl]benzoate 3 g (6.1 mmol) of 4-[7-(1-adamantyl)-6-methoxyethoxymethoxy-2-naphthyl]benzoic acid and 100 ml of DMF were introduced into a three-necked flask under a stream of nitrogen. 200 mg (6.7 mmol) of sodium hydride (80% in oil) were added portionwise and stirring was carried out until gas evolution had ceased. 500 μl (6.1 mmol) of iodopropane were then added and the reaction mixture was stirred for one hour. The reaction mixture was poured into water and extracted with ethyl acetate and the organic phase was separated by settling, dried over magnesium sulfate and evaporated.

The residue obtained was purified by chromatography on a silica column and eluted with a mixture of heptane and ethyl acetate (80/20). 1 g (33%) of the propyl ester was collected, which ester had a melting point of 121°–2° C.

EXAMPLE 33

Preparation of 4-[7-(1-adamantyl)-6-methoxyethoxymethoxy-2-naphthyl]phenyl acetate Following the procedure of Example 1(c), but reacting 5 g (12.8 mmol) of 7-(1-adamantyl)-6-methoxyethoxy-methoxy-2-naphthylboronic acid with 2.7 g (10.1 mmol) of 4-iodophenyl acetate, 2.88 g (57%) of the expected compound were obtained, which compound had a melting point of 117°–8° C.

EXAMPLE 34

Preparation of 4-[7-(1-adamantyl)-6-methoxyethoxymethoxy-2-naphthyl]phenol

Following the procedure of Example 1(d), from 2.5 g (5 mmol) of 4-[7-(1-adamantyl)-6-methoxyethoxymethoxy-2-naphthyl]phenyl acetate, 2.2 g (97%) of 4-[7-(1-adamantyl)-6-methoxyethoxymethoxy-2-naphthyl]phenol were obtained, which compound had a melting point of 126°–7° C.

EXAMPLE 35

Preparation of 4-[7-(1-adamantyl)-6-methoxyethoxymethoxy-2-naphthyl] phenoxyethylmorpholine hydrochloride 600 mg (1.32 mmol) of 4-[7-(1-adamantyl)-6-methoxyethoxymethoxy-2-naphthyl]phenol, 550 mg (3.96 mmol) of potassium carbonate, 4 mg of potassium iodide and 60 ml of methyl ethyl ketone were introduced into a round-bottomed flask under a stream of nitrogen. 270 mg (1.45 mmol) of 4-(2-chloroethyl)morpholine hydrochloride were added and the reaction mixture was heated at reflux for twelve hours. The reaction mixture was poured into 1N hydrochloric acid and extracted with ethyl ether and the organic phase was separated by settling, dried over magnesium sulfate and evaporated.

The residue obtained was purified by chromatography on a silica column and eluted with ethyl acetate. After evaporation of the solvents, an oil was collected. The hydrochloride was formed by dissolving the oil in ethyl ether and by then adding 1 ml of a saturated solution of HCl in methanol. The salt was filtered and dried and 350 mg (44%) of the expected hydrochloride were collected, which compound had a melting point of 123°–4° C.

EXAMPLE 36

Preparation of 4-[7-(1-adamantyl)-6-methoxyethoxymethoxy-2-naphthyl] henoxyethylpiperidine hydrochloride Following the procedure of Example 35, but reacting 600 mg (1.32 mmol) of 4-[7-(1-adamantyl)-6-methoxy-ethoxymethoxy-2-naphthyl]phenol with 310 mg (1.7 mmol) of 1-(2-chloroethyl)piperidine hydrochloride, 770 mg (85%) of the expected hydrochloride were obtained, which compound had a melting point of 126°–7° C.

EXAMPLE 37

Preparation of hexyl 4-[7-(1-adamantyl)-6-methoxyethoxymethoxy-2-naphthyl]benzoate Following the procedures of Example 32, but reacting 1.35 g (2.8 mmol) of 4-[7-(1-adamantyl)-6-methoxy-ethoxymethoxy-2-naphthyl]benzoic acid with 800 μl (5.6 mmol) of iodohexane, 980 mg (62%) of the hexyl ester were obtained, which ester had a melting point of 73°–4° C.

EXAMPLE 38

Preparation of N-[[4-[7-(1-adamantyl)-6-methoxyethoxymethoxy-2-naphthyl]benzoyl]] glutamic acid (a) Preparation of diethyl N-[[4-[7-(1-adamantyl)-6-methoxyethoxy-methoxy-2-naphthyl]benzoyl]] glutamate 1.93 g (7.8 mmol) of diethyl L-glutamate hydrochloride, 1.13 g (9.24 mmol) of 4-dimethylamino-pyridine and 100 ml of THF were introduced into a round-bottomed flask. A solution of 3.59 g (7.1 mmol) of 4-[7-(1-adamantyl)-6-methoxyethoxymethoxy-2-naphthyl]benzoic acid chloride in THF was added dropwise and the reaction mixture was stirred at room temperature for four hours. The reaction mixture was poured into water and extracted with ethyl acetate and the organic phase was separated by settling, dried over magnesium sulfate and evaporated.

The residue obtained was purified by chromatography on a silica column and eluted with a mixture of heptane and ethyl acetate (70/30). 2.8 g (58%) of the expected compound were collected in the form of an oil.

(b) Synthesis N-[[4-[7-(1-adamantyl)-6-methoxyethoxymethoxy-2-naphthyl]benzoyl]] glutamic acid Following the product of Example 1(d), from 2.7 g (4.2 mmol) of the above diester, 1.45 g (56%) of N-[[4-[7-(1-adamantyl)-6-methoxyethoxymethoxy-2-naphthyl]benzoyl]]glutamic acid were obtained, which acid had a melting point of 137°–8° C.

EXAMPLE 39

Preparation of 4-[7-(1-adamantyl)-6-methoxyhexyloxy-2-naphthyl]benzoic acid (a) Preparation of methyl 4-[7-(1-adamantyl)-6-methoxyhexyloxy-2-naphthyl]benzoate Following the procedure of Example 12(a), but reacting 870 mg (1.7 mmol) of methyl 4-[7-(1-adamantyl)-6-hydroxyhexyloxy-2-naphthyl]benzoate with 160 μl (1.7 mmol) of dimethyl sulphate, 100 mg (14%) of the expected compound were obtained, which compound had a melting point of 141°–3° C.

(b) Synthesis of 4-[7-(1-adamantyl)-6-methoxyhexyloxy-2-naphthyl]benzoic acid

Following the procedure of Example 1(d), from 95 mg (0.18 mmol) of the ester prepared in step (a), 61 mg (66%)

of the expected acid were obtained, which acid had a melting point of 267°–9° C.

EXAMPLE 40

Preparation of 4-[7-(1-adamantyl)-6-methoxymethoxypropyl-2-naphthyl]benzoic acid (a) Preparation of methyl 4-[7-(1-adamantyl)-6-methoxymethoxypropyl-2-naphthyl]benzoate 541 mg (1.2 mmol) of methyl 4-[7-(1-adamantyl)-6-hydroxypropyl-2-naphthyl]benzoate and 5 ml of dimethoxymethane were introduced into a round-bottomed flask and 5 drops of trimethylsilyl iodide were added. The reaction mixture was stirred at room temperature for 24 hours, was poured into water and extracted with ethyl ether and the organic phase was separated by settling, dried over magnesium sulfate and evaporated.

The residue obtained was purified by chromatography on a silica column and eluted with a mixture of dichloromethane and heptane (70/30). 355 mg (59%) of the expected compound were collected, which compound had a melting point of 137°–8° C.

(b) Synthesis of 4-[7-(1-adamantyl)-6-methoxymethoxypropyl-2-naphthyl]benzoic acid Following the procedure of Example 1(d), from 345 mg (0.69 mmol) of the ester prepared in step (a), 280 mg (83%) of the expected acid were obtained, which acid had a melting point of 237°–8° C.

EXAMPLE 41

Preparation of 4-[7-(1-adamantyl)-6-methoxymethoxyethyl-2-naphthyl]benzoic acid (a) Preparation of methyl 4-[7-(1-adamantyl)-6-methoxymethoxyethyl-2-naphthyl]benzoate Following the procedure of Example 40(a), from 200 mg (0.47 mmol) of methyl 4-[7-(1-adamantyl)-6-hydroxy-ethyl-2-naphthyl]benzoate, 156 mg (68%) of the expected compound were obtained, which compound had a melting point of 145°–6° C.

(b) Synthesis of 4-[7-(1-adamantyl)-6-methoxymethoxyethyl-2-naphthyl]benzoic acid Following the procedure of Example 1(d), from 149 mg (0.3 mmol) of the ester prepared in step (a), 101 mg (70%) of the expected acid were obtained, which acid had a melting point of 225°–7° C.

EXAMPLE 42

The antagonist activity of the compounds of formula (I) was evaluated in the test of differentiation of embryonic teratocarcinoma F9 cells in mice (*Cancer Research*, 43, p. 5268 (1983)).

These compounds, tested at $10^{-6}$M, were inactive as agonists in this test and partially or completely inhibit the effect elicited by an agonist retinoid on the morphology and on the secretion of the activator of plasminogen according to the following protocol.

The F9 cells were inoculated in 12-well clusters and the compounds were tested from $10^{-9}$ to $10^{-5}$M in the presence of all-trans-retinoic acid or of a synthetic agonist retinoid (compound A): 4-(5,6,7,8-tetrahydro-5,5,8,8-tetramethyl-2-naphthylaminomethyl]benzoic acid (BASF) at $10^{-8}$M.

After incubating for three days, the morphological observations were carried out and the concentration of the tested compound ($IC_{50}$) which inhibited the effect of the agonist on the secretion of the activator of plasminogen by 50% was determined.

| Example | Antagonist against compound A (10 nM) Test of differentiation of F9 cells $IC_{50}$ (nM) |
|---|---|
| 1 | 5 |
| 3 | 2 |
| 5 | 180 |
| 6 | 500 |
| 14 | 250 |
| 20 | 100 |
| 39 | 450 |

EXAMPLE 43

In this example, various specific formulations based on the compounds according to the invention are illustrated.

(A) ORAL ROUTE:

(a) 0.2 g Tablet:

| | | |
|---|---|---|
| (i) Compound prepared in Example 6 | 0.001 | g |
| (ii) Starch | 0.114 | g |
| (iii) Dicalcium phosphate | 0.020 | g |
| (iv) Silica | 0.020 | g |
| (v) Lactose | 0.030 | g |
| (vi) Talc | 0.010 | g |
| (vii) Magnesium stearage | 0.005 | g |

(b) Drinkable suspension in 5 ml ampoules:

| | | |
|---|---|---|
| (i) Compound prepared in Example 5 | 0.001 | g |
| (ii) Glycerol | 0.500 | g |
| (iii) 70% Sorbitol | 0.500 | g |
| (iv) Sodium saccharinate | 0.010 | g |
| (v) Methyl para-hydroxybenzoate | 0.040 | g |
| (vi) Flavoring q.s. | | |
| (vii) Purified water q.s. for | 5 | ml |

(c) 0.8 g Tablet:

| | | |
|---|---|---|
| (i) Compound of Example 2 | 0.500 | g |
| (ii) Pregelatinized starch | 0.100 | g |
| (iii) Microcrystalline cellulose | 0.115 | g |
| (iv) Lactose | 0.075 | g |
| (v) Magnesium stearate | 0.010 | g |

(d) Drinkable suspension in 10 ml ampoules:

| | | |
|---|---|---|
| (i) Compound of Example 4 | 0.200 | g |
| (ii) Glycerol | 1.000 | g |
| (iii) 70% Sorbitol | 1.000 | g |
| (iv) Sodium saccharinate | 0.010 | g |
| (v) Methyl para-hydroxybenzoate | 0.080 | g |
| (vi) Flavoring q.s. | | |
| (v) Purified water q.s. for | 10 | ml |

(B) TOPICAL ROUTE:

(a) Ointment:

| | | |
|---|---|---|
| (i) Compound of Example 6 | 0.020 | g |
| (ii) Isopropyl myristate | 81.700 | g |
| (iii) Fluid paraffin oil | 9.100 | g |
| (iv) Silica ("Aerosil 200" marketed by Degussa) | 9.180 | g |

(b) Ointment:

| | | |
|---|---|---|
| (i) Compound of Example 2 | 0.300 | g |
| (ii) Pharmaceutical-grade white petroleum jelly q.s. for | 100 | g |

-continued (c) Non-ionic water-in-oil cream:

| | | |
|---|---|---|
| (i) Compound of Example 7 | 0.100 g | |
| (ii) Mixture of emulsified lanolin alcohols, of waxes and of oils ("Anhydrous eucerin" marketed by BDF) | 39.900 g | |
| (iii) Methyl para-hydroxybenzoate | 0.075 g | |
| (iv) Propyl para-hydroxybenzoate | 0.075 g | |
| (v) Sterile demineralized water q.s. for | 100 g | |

(d) Lotion:

| | | |
|---|---|---|
| (i) Compound of Example 8 | 0.100 g | |
| (ii) Polyethylene glycol (PEG 400) | 69.900 g | |
| (iii) 95% Ethanol | 30.000 g | |

(e) Hydrophobic ointment:

| | | |
|---|---|---|
| (i) Compound of Example 10 | 0.300 g | |
| (ii) Isopropyl myristate | 36.400 g | |
| (iii) Silicone oil ("Rhodorsil 47 V 300" marketed by Rhône-Poulenc) | 36.400 g | |
| (iv) Beeswax | 13.600 g | |
| (v) Silicone oil ("Abil 300.000 cst" marketed by Goldschmidt) q.s. for | 100 g | |

(f) Non-ionic oil-in-water cream:

| | | |
|---|---|---|
| (i) Compound of Example 5 | 1.000 g | |
| (ii) Cetyl alcohol | 4.000 g | |
| (iii) Glyceryl monostearate | 2.500 g | |
| (iv) PEG 50 stearate | 2.500 g | |
| (v) Karite butter | 9.200 g | |
| (vi) Propylene glycol | 2.000 g | |
| (v) Methyl para-hydroxybenzoate | 0.075 g | |
| (vi) Propyl para-hydroxybenzoate | 0.075 g | |
| (vii) Sterile demineralized water q.s. for | 100 g | |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A pharmaceutical composition comprising a prophylactically or therapeutically effective amount of at least one adamantyl-substituted retinoid compound having the structural formula (I) which possesses RAR-antagonist type activity:

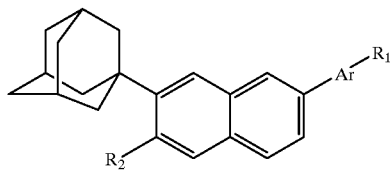

(1)

in which $R_1$ is (i) the $-CH_3$ radical, (ii) the $-CH_2OH$ radical, (iii) an $-O-R_3$ radical, or (iv) a $-CO-R_4$ radical, wherein $R_3$ and $R_4$ are as defined below; Ar is a radical:

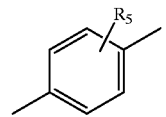

(a)

wherein $R_5$ is as defined below; $R_2$ is an $-(X)_n-(CH_2)_p-R_6$ radical, an $-(X)_n-(CH_2)_q-R_7$ radical, a $-CH=CH-(CH_2)_s-R_6$ radical, or a $-CH=CH-(CH_2)_t-R_7$ radical, wherein $R_6$, $R_7$, X, n, p, q, s and t are as defined below; $R_3$ is a hydrogen atom, a lower alkyl radical, or a $-(CH_2)_m-(CO)_n-R_8$ radical, wherein $R_8$, m and n are as defined below; $R_4$ is a hydrogen atom, a lower alkyl radical, a radical of the formula:

or an $-OR_9$ radical, wherein R', R" and $R_9$ are as defined below; $R_5$ is a hydrogen or halogen atom, a linear or branched alkyl radical having from 1 to 20 carbon atoms, a hydroxyl radical or an $-OR_{10}$ or $-OCOR_{10}$ radical, wherein $R_{10}$ is as defined below; $R_6$ is a hydrogen atom, a linear or branched alkyl radical having from 1 to 20 carbon atoms, an alkenyl radical, or an alkynyl radical; $R_7$ is an aryl radical, a mono- or polyhydroxyalkyl radical in which the hydroxyl moieties are optionally protected in the methoxy or acetoxy or acetonide form, an aminoalkyl radical in which the amine functional group is optionally substituted by one or two lower alkyl radicals, a polyether radical, a $-COR_4$ radical, a saturated or unsaturated heterocycle, or an aminoaryl radical; $R_8$ is a lower alkyl radical or a saturated heterocycle; $R_9$ is a hydrogen atom, a linear or branched alkyl radical having from 1 to 20 carbon atoms, an alkenyl radical, a mono- or polyhydroxyalkyl radical, an optionally substituted aryl or aralkyl radical, or a sugar residue or an amino acid or peptide residue; $R_{10}$ is a lower alkyl radical; X is an oxygen atom or an $-S(O)_r$ radical; R' and R", which may be identical or different, are each a hydrogen atom, a lower alkyl radical, a mono- or polyhydroxyalkyl radical, an optionally substituted aryl radical, or an amino acid, peptide or sugar residue, or alternatively, taken together, form a saturated heterocycle, with the proviso that R' and R" may together form, with the nitrogen atom from which they depend, a saturated heterocycle; m is an integer ranging from 1 to 3, inclusive; n is an integer ranging from 0 to 1, inclusive; p is an integer ranging from 5 to 12, inclusive; q is an integer ranging from 0 to 12, inclusive; r is an integer ranging from 0 to 2, inclusive; s is an integer ranging from 3 to 10, inclusive; t is an integer ranging from 0 to 10 inclusive; or a pharmaceutically acceptable salt or optical or geometric isomer thereof, wherein said composition is effective for the treatment of a disorder or ailment relating to over-regulation of RAR receptors and/or to hypervitaminosis A.

2. The composition of claim 1, where in said at least one adamantyl-substituted retinoid compound comprises a pharmaceutically acceptable salt thereof.

3. The composition of claim 1, where in said at least one adamantyl-substituted retinoid compound of formula (I), the said lower alkyl radical substituents are selected from among methyl, ethyl, isopropyl, butyl, tert-butyl and hexyl radicals.

4. The composition of claim 1, where in said at least one adamantyl-substituted retinoid compound of formula (I), said linear or branched alkyl radical substituents having from 1 to 20 carbon atoms are selected from among methyl, ethyl, propyl, 2-ethylhexyl, octyl, dodecyl, hexadecyl and octadecyl radicals.

5. The composition of claim 1, where in said at least one adamantyl-substituted retinoid compound of formula (I), said monohydroxyalkyl radical substituents are selected from among hydroxymethyl, 2-hydroxyethyl, 2-hydroxypropyl and 3-hydroxypropyl radicals.

6. The composition of claim 1, where in said at least one adamantyl-substituted retinoid compound of formula (I), said polyhydroxyalkyl radical substituents are selected from among 2,3-dihydroxypropyl, 2,3,4-trihydroxybutyl, 2,3,4,5-tetrahydroxy-pentyl and pentaerythritol radicals.

7. The composition of claim 1, where in said at least one adamantyl-substituted retinoid compound of formula (I), said aryl radical substituents are selected from among phenyl radicals optionally substituted by at least one halogen atom, or by at least one hydroxyl or nitro functional group.

8. The composition of claim 1, where in said at least one adamantyl-substituted retinoid compound of formula (I), said aralkyl radical substituents are selected from among benzyl and phenethyl radicals optionally substituted by at least one halogen atom, or by at least one hydroxyl or nitro functional group.

9. The composition of claim 1, where in said at least one adamantyl-substituted retinoid compound of formula (I), said alkenyl radical substituents have from 2 to 5 carbon atoms and comprise at least one site of ethylenic unsaturation.

10. The composition of claim 1, where in said at least one adamantyl-substituted retinoid compound of formula (I), said sugar residue substituents are selected from among those of glucose, galactose, mannose and glucuronic acid.

11. The composition of claim 1, where in said at least one adamantyl-substituted retinoid compound of formula (I), said amino acid residue substituents are selected from among those of lysine, glycine and aspartic acid.

12. The composition of claim 1, where in said at least one adamantyl-substituted retinoid compound of formula (I), said peptide residue substituents are those of a dipeptide or tripeptide.

13. The composition of claim 1, where in said at least one adamantyl-substituted retinoid compound of formula (I), said halogen atom substituents are selected from among fluorine, chlorine and bromine atoms.

14. The composition of claim 1, where in said at least one adamantyl-substituted retinoid compound is selected from among 2-hydroxy-4-[7-(1-adamantyl)-6-benzyloxy-2-naphthyl]benzoic acid; 2-hydroxy-4-[7-(1-adamantyl)-6-hexyloxy-2-naphthyl]benzoic acid; 4-[7-(1-adamantyl)-6-methoxyethoxymethoxy-2-naphthyl]benzoic acid; 5-[7-(1-adamantyl)-6-benzyloxy-2-naphthyl]-2-thiophenecarboxylic acid; 4-[7-(1-adamantyl)-6-benzyloxy-2-naphthyl]benzoic acid; 4-[7-(1-adamantyl)-6-benzyloxycarbonyl-2-naphthyl]benzoic acid; 2- hydroxy-4-[7-(1-adamantyl)-6-(4-fluorobenzyl)oxy-2-naphthyl]benzoic acid; 6-[7-(1-adamantyl)-6-methoxyethoxymethoxy-2-naphthyl]nicotinic acid; 4-[7-(1-adamantyl)-6-heptyloxy-2-naphthyl]-benzoic acid; 2-hydroxy-4-[7-(1-adamantyl)-6-methoxyethoxy-methoxy-2-naphthyl]benzoic acid; 2-chloro-4-[7-(1-adamantyl)-6-methoxyethoxymethoxy-2-naphthyl]benzoic acid; 4-[7-(1-adamantyl)-6-hydroxyhexyloxy-2-naphthyl]benzoic acid; 4-[7-(1-adamantyl)-6-hydroxypropyl-2-naphthyl]benzoic acid; 4-[7-(1-adamantyl)-6-hydroxyoctyloxy-2-naphthyl] benzoic acid; 4-[7-(1-adamantyl)-6-hydroxyethyl-2-naphthyl]benzoic acid; 4-[7-(1-adamantyl)-6-hydroxyheptyloxy-2-naphthyl]benzoic acid; 4-[7-(1-adamantyl)-6-hydroxypentyloxy-2-naphthyl]benzoic acid; 4-[7-(1-adamantyl)-6-(4-morpholino)ethyloxy-2-naphthyl]benzoic acid; 4-[7-(1-adamantyl)-6-(1-piperidino)ethyloxy-2-naphthyl]benzoic acid; 4-[7-(1-adamantyl)-6-carbonylpentyloxy-2-naphthyl]benzoic acid; 4-[7-(1-adamantyl)-6-ethoxycarbonylpentyloxy-2-naphthyl]benzoic acid; 4-[7-(1-adamantyl)-6-ethoxycarbonylbutyloxy-2-naphthyl]benzoic acid; 4-[7-(1-adamantyl)-6-carboxypentyloxy-2-naphthyl]benzoic acid; 4-[7-(1-adamantyl)-6-carboxybutyloxy-2-naphthyl]benzoic acid; 4-[7-(1-adamantyl)-6-methoxyethoxy-methoxy-2-naphthyl]benzenemethanol; 4-[7-(1-adamantyl)-6-methoxyethoxymethoxy-2-naphthyl]benzaldehyde; 4-[7-(1-adamantyl)-6-methoxyethoxymethoxy-2-naphthyl]benzoic acid morpholide; N-ethyl-4-[7-(1-adamantyl)-6-methoxyethoxymethoxy-2-naphthyl]benzamide; 4-[7-(1-adamantyl)-6-methoxyethoxymethoxy-2-naphthyl]benzamide; N-(4-hydroxyphenyl)-4-[7-(1-adamantyl)-6-methoxyethoxymethoxy-2-naphthyl]benzamide; 4-[7-(1-adamantyl)-6-methoxyethoxymethoxy-2-naphthyl]benzoylpiperazine; propyl 4-[7-(1-adamantyl)-6-methoxyethoxymethoxy-2-naphthyl]benzoate; 4-[7-(1-adamantyl)-6-methoxyethoxymethoxy-2-naphthyl]phenyl acetate; 4-[7-(1-adamantyl)-6-methoxyethoxymethoxy-2-naphthyl]-phenol; 4-[7-(1-adamantyl)-6-methoxyethoxymethoxy-2-naphthyl]-phenoxyethylmorpholine hydrochloride; 4-[7-(1-adamantyl)-6-methoxyethoxymethoxy-2-naphthyl] phenoxyethylpiperidine hydrochloride; hexyl 4-[7-(1-adamantyl)-6-methoxyethoxymethoxy-2-naphthyl] benzoate; N-[[4-[7-(1-adamantyl)-6-methoxyethoxymethoxy-2-naphthyl]benzoyl]]glutamic acid; 4-[7-(1-adamantyl)-6-methoxyhexyloxy-2-naphthyl]benzoic acid; 4-[7-(1-adamantyl)-6-methoxymethoxypropyl-2-naphthyl] benzoic acid; and 4-[7-(1-adamantyl)-6-methoxymethoxyethyl-2-naphthyl]benzoic acid.

15. The composition of claim 1, where in said at least one adamantyl-substituted retinoid compound of formula (I), wherein $R_1$ is a —CO—$R_4$ radical, $R_2$ is a —$(X)_n$—$(CH_2)_p$—$R_6$ or $(X)_n$—$CH_2)_q$—$R_7$ radical and Ar is a radical (a).

16. The composition of claim 1, where in said at least one adamantyl-substituted retinoid compound of formula (I), wherein $R_7$ is a polyether radical having a carbon in the position a to the carbon which is in the 6-position of the naphthyl radical.

17. The composition of claim 1, where in said at least one adamantyl-substituted retinoid compound is 4-[7-(1-adamantyl)-6-methoxymethoxypropyl-2-naphthyl]benzoic acid.

18. The composition of claim 1, where in said at least one adamantyl-substituted retinoid compound is 4-[7-(1-adamantyl)-6-methoxymethoxyethyl-2-naphthyl]benzoic acid.

19. The pharmaceutical composition of claim 1, comprising a therapeutically effective amount of said at least one adamantyl-substituted retinoid compound, or pharmaceutically acceptable salt or isomer thereof, and a pharmaceutically acceptable vehicle, carrier or diluent therefor.

20. The pharmaceutical composition as defined by claim 19, further comprising another retinoid compound, a D vitamin or derivative thereof, a corticosteroid, an anti-free radical agent, an α-hydroxy or α-keto acid or derivative thereof, an ion channel blocker, or combination thereof.

21. The pharmaceutical composition as defined by claim 19, comprising a tablet, a capsule, a syrup, a dragee, a suspension, an elixir, a solution, a powder, granules, an emulsion, microspheres, nanospheres, lipid vesicles, polymeric vesicles, or an injectable.

22. The pharmaceutical composition as defined by claim 19, comprising an ointment, a cream, a milk, a salve, an impregnated pad, a gel, a spray, or a lotion.

23. The pharmaceutical composition as defined by claim 19, adopted for topical administration.

24. The pharmaceutical composition as defined by claim 19, adopted for systemic administration.

25. The pharmaceutical composition as defined by claim 19, comprising from 0.001% to 5% by weight of said adamantyl-substituted retinoid compound, or salt or isomer thereof.

26. A method for treating a keratinization disorder in a mammalian organism in need of such treatment, comprising administering to such organism a therapeutically effective amount of the pharmaceutical composition as defined by claim 19.

27. A method for treating a dermatological disorder in a mammalian organism in need of such treatment, comprising administering to such organism a therapeutically effective amount of the pharmaceutical composition as defined by claim 19.

28. A method for treating a ophthalmological disorder selected from corneopathies in a mammalian organism in need of such treatment, comprising administering to such organism a therapeutically effective amount of the pharmaceutical composition as defined by claim 19.

29. A method for treating skin aging in a mammalian organism in need of such treatment, comprising administering to such organism a therapeutically effective amount of the pharmaceutical composition as defined by claim 19.

30. A method for treating epidermal and/or dermal atrophy in a mammalian organism in need of such treatment, comprising administering to such organism a therapeutically effective amount of the pharmaceutical composition as defined by claim 19.

31. A method for treating a healing disorder in a mammalian organism in need of such treatment, comprising administering to such organism a therapeutically effective amount of the pharmaceutical composition as defined by claim 19.

32. A method for treating a sebaceous function disorder in a mammalian organism in need of such treatment, comprising administering to such organism a therapeutically effective amount of the pharmaceutical composition as defined by claim 19.

33. A method for treating skin cancer in a mammalian organism in need of such treatment, comprising administering to such organism a therapeutically effective amount of the pharmaceutical composition as defined by claim 19.

34. A method for treating a viral infection selected from HIV-I or hepatitis B in a mammalian organism in need of such treatment, comprising administering to such organism a therapeutically effective amount of the pharmaceutical composition as defined by claim 19.

35. A method for treating a disorder and/or ailment manifesting an overregulation of RAR receptors and/or a hypervitaminosis A in a mammalian organism in need of such treatment, comprising administering to such organism a therapeutically effective amount of the pharmaceutical composition as defined by claim 19.

36. The method as defined by claim 35, comprising administering to such organism a daily dose of said adamantyl-substituted retinoid compound of about 0.01 mg/kg to 100 mg/kg of body weight thereof.

37. A cosmetic composition of matter, comprising a cosmetically effective amount of an adamantyl-substituted retinoid compound as defined by claim 1, or cosmetically acceptable salt or isomer thereof, and a cosmetically acceptable vehicle, carrier or diluent therefor.

38. The cosmetic composition as defined by claim 37, comprising a cream, a milk, a lotion, a gel, an ointment, microspheres, nanospheres, lipid vesicles, polymeric vesicles, a soap, or a shampoo.

39. The cosmetic composition as defined by claim 37, comprising from 0.001% to 3% by weight of said adamantyl-substituted retinoid compound, or salt or isomer thereof.

40. The cosmetic composition as defined by claim 37, further comprising another retinoid compound, a D vitamin or derivative thereof, a corticosteroid, an anti-free radical agent, an α-hydroxy or α-keto acid or derivative thereof, an ion channel blocker, or combination thereof.

41. The pharmaceutical composition as defined by claim 19, further comprising a wetting agent, a depigmenting agent, a moisturizing agent, an emollient, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

42. The pharmaceutical composition as defined by claim 19, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

43. The cosmetic composition by claim 37, further comprising a wetting agent, a depigmenting agent, a moisturizing agent, an emollient, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

44. The cosmetic composition as defined by claim 37, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

45. A method for treating a disorder or ailment related to overregulation of RAR receptors and/or to hypervitaminosis A comprising administering a therapeutically effective amount of an adamantyl-substituted retinoid compound according to claim 1.

46. A method for treating a disorder or ailment related to overregulation of RAR receptors and/or to hypervitaminosis A comprising administering a therapeutically effective amount of an adamantyl-substituted retinoid compound as set forth in claim 14.

47. The adamantyl-substituted retinoid compound of Formula (I), wherein Ar is radical (a) as defined in claim 1, wherein $R_7$ is a polyether radical having a carbon in the position α to the carbon atom which is in the 6th position of the naphthyl radical.

48. An adamantyl-substituted retinoid compound according to claim 47, which is selected from the group consisting of 4-[7-(1-adamantyl)-6-methoxymethoxypropyl-2-naphthyl]benzoic acid and 4-[7-(1-adamantyl)-6-methoxymethoxyethyl-2-naphthyl]benzoic acid.

49. A method for treating a disorder or ailment relating to the over-regulation of RAR receptors and/or to hypervitaminosis A comprising administering a therapeutically effective amount of an adamantyl-substituted retinoid compound according to claim 47.

50. A method for treating a disorder or ailment relating to over-regulation of RAR receptors and/or to hypervitaminosis A comprising administering a therapeutically effective amount of an adamantyl-substituted retinoid compound according to claim 48.

51. The composition of claim 1, wherein a saturated heterocycle refers to a heterocycle radical selected from the group consisting of piperidino, morpholino, pyrrolidino, and piperazino, optionally substituted at the 4 position by a $C_1$–$C_6$ alkyl or mono- or polyhydroxyalkyl radical, and an unsaturated heterocycle refers to a heterocycle radical selected from pyridine, furan and thiophene radical.

52. The method of claim 49, wherein said disorder ailment is selected from the group consisting of acne vulgaris, comedonic or polymorphic acne, acne rosacea, nodulocystic acne, acne conglobata, senile acne, secondary acnes selected from the group consisting of solar, medicinal and occupational acne, ichthyoses, ichthyosiform conditions, Darrier's disease, palinoplantar keratoderma, leucoplakia conditions, leucoplakiform conditions, cutaneous or mucosal lichen, psoriasis, psoriatic rheumatism, cutaneous atopy, eczema, respiratory atopy, gingival hypertrophy, arthritis, dermal or epidermal proliferations, malignant or benign, common warts, flat warts, epidermodysplasia verruciformis, florid or oral papillomatoses, proliferations induced by ultraviolet radiation, bullous dermatoses, collagen diseases, corneopathies, skin aging, actinic keratoses, pigmentations or pathologies associated with chronologic or actinic aging, stigmata of epidermal and/or dermal atrophy induced by local or systemic corticosteroids, healing or stretch marks, disorders of the sebaceous function.

53. The method according to claim 49, wherein said disorder or ailment is psoriasis.

* * * * *